US012646601B2

(12) United States Patent
Narayanaswami

(10) Patent No.: US 12,646,601 B2
(45) Date of Patent: Jun. 2, 2026

(54) INSULIN ADAPTATION AND SAFETY MONITORING

(71) Applicant: INSULET CORPORATION, Acton, MA (US)

(72) Inventor: Rangarajan Narayanaswami, Weston, MA (US)

(73) Assignee: INSULET CORPORATION, Acton, MA (US)

( * ) Notice: Subject to any disclaimer, the term of this patent is extended or adjusted under 35 U.S.C. 154(b) by 445 days.

(21) Appl. No.: 18/137,179

(22) Filed: Apr. 20, 2023

(65) Prior Publication Data

US 2023/0338644 A1 Oct. 26, 2023

Related U.S. Application Data

(60) Provisional application No. 63/333,149, filed on Apr. 21, 2022.

(51) Int. Cl.
| | |
|---|---|
| *G16H 20/10* | (2018.01) |
| *A61B 5/145* | (2006.01) |
| *A61M 5/172* | (2006.01) |
| *A61M 5/142* | (2006.01) |

(52) U.S. Cl.
CPC ......... *G16H 20/10* (2018.01); *A61B 5/14532* (2013.01); *A61B 5/14546* (2013.01); *A61M 5/1723* (2013.01); *A61M 5/14248* (2013.01); *A61M 2202/0486* (2013.01); *A61M 2205/3303* (2013.01); *A61M 2205/502* (2013.01); *A61M 2205/52* (2013.01); *A61M 2230/201* (2013.01)

(58) Field of Classification Search
CPC ........ G16H 20/10; G16H 20/30; G16H 20/60; G16H 40/67; G16H 50/20; G16H 50/30; G16H 20/17; A61B 5/14532; A61B 5/14546; A61M 5/14248; A61M 5/1723; A61M 2202/0486; A61M 2205/3303; A61M 2205/502; A61M 2205/52; A61M 2230/201

See application file for complete search history.

(56) References Cited

U.S. PATENT DOCUMENTS

| 303,013 A | 8/1884 | Horton |
|---|---|---|
| 441,663 A | 12/1890 | Hofbauer |
| 445,545 A | 2/1891 | Crane |

(Continued)

FOREIGN PATENT DOCUMENTS

| AU | 2015200834 A1 | 3/2015 |
|---|---|---|
| AU | 2015301146 A1 | 3/2017 |

(Continued)

OTHER PUBLICATIONS

US 5,954,699 A, 09/1999, Jost et al. (withdrawn)

(Continued)

*Primary Examiner* — William H Rodriguez
(74) *Attorney, Agent, or Firm* — Goodwin Procter LLP

(57) ABSTRACT

Disclosed are a system, techniques and processes for monitoring and modifying a drug treatment regimen when a user partakes in a ketogenic diet. The disclosed system obtains ketone level measurements of a user and indicates a user's adherence to the ketogenic diet as well as modifying a user's total daily dosage of a drug based on the user's following the ketogenic diet.

20 Claims, 10 Drawing Sheets

(56) References Cited

U.S. PATENT DOCUMENTS

| | | |
|---|---|---|
| 588,583 A | 8/1897 | Lade |
| 955,911 A | 4/1910 | Saegmuller |
| 1,441,508 A | 1/1923 | Jensen |
| 2,283,925 A | 5/1942 | Harvey |
| 2,797,149 A | 6/1957 | Skeggs |
| 2,886,529 A | 5/1959 | Guillaud |
| 3,574,114 A | 4/1971 | Monforte |
| 3,614,554 A | 10/1971 | Shield |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,885,662 A | 5/1975 | Schaefer |
| 3,963,380 A | 6/1976 | Thomas, Jr. et al. |
| 3,983,077 A | 9/1976 | Fuller et al. |
| 4,055,175 A | 10/1977 | Clemens et al. |
| 4,108,177 A | 8/1978 | Pistor |
| 4,146,029 A | 3/1979 | Ellinwood, Jr. |
| 4,151,845 A | 5/1979 | Clemens |
| 4,206,401 A | 6/1980 | Meyer |
| 4,245,634 A | 1/1981 | Albisser et al. |
| 4,268,150 A | 5/1981 | Chen |
| 4,277,226 A | 7/1981 | Archibald |
| 4,307,713 A | 12/1981 | Galkin et al. |
| 4,313,439 A | 2/1982 | Babb et al. |
| 4,368,980 A | 1/1983 | Aldred et al. |
| 4,373,527 A | 2/1983 | Fischell |
| 4,398,542 A | 8/1983 | Cunningham et al. |
| 4,400,683 A | 8/1983 | Eda et al. |
| 4,403,984 A | 9/1983 | Ash et al. |
| 4,424,720 A | 1/1984 | Bucchianeri |
| 4,435,173 A | 3/1984 | Siposs et al. |
| 4,464,170 A | 8/1984 | Clemens et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,523,170 A | 6/1985 | Huth, III |
| 4,526,568 A | 7/1985 | Clemens et al. |
| 4,526,569 A | 7/1985 | Bernardi |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,573,968 A | 3/1986 | Parker |
| 4,585,439 A | 4/1986 | Michel |
| 4,587,850 A | 5/1986 | Moser |
| 4,601,707 A | 7/1986 | Albisser et al. |
| 4,624,661 A | 11/1986 | Arimond |
| 4,633,878 A | 1/1987 | Bombardieri |
| 4,634,427 A | 1/1987 | Hannula et al. |
| 4,646,038 A | 2/1987 | Wanat |
| 4,657,529 A | 4/1987 | Prince et al. |
| 4,678,408 A | 7/1987 | Nason et al. |
| 4,684,368 A | 8/1987 | Kenyon |
| 4,685,903 A | 8/1987 | Cable et al. |
| 4,731,726 A | 3/1988 | Allen, III |
| 4,743,243 A | 5/1988 | Vaillancourt |
| 4,755,169 A | 7/1988 | Sarnoff et al. |
| 4,755,173 A | 7/1988 | Konopka et al. |
| 4,759,120 A | 7/1988 | Bernstein |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,850,954 A | 7/1989 | Charvin |
| 4,854,170 A | 8/1989 | Brimhall et al. |
| 4,859,492 A | 8/1989 | Rogers, Jr. et al. |
| 4,880,770 A | 11/1989 | Mir et al. |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,944,659 A | 7/1990 | Labbe et al. |
| 4,961,055 A | 10/1990 | Habib et al. |
| 4,967,201 A | 10/1990 | Rich, III |
| 4,969,874 A | 11/1990 | Michel et al. |
| 4,973,998 A | 11/1990 | Gates |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,007,458 A | 4/1991 | Marcus et al. |
| 5,045,871 A | 9/1991 | Reinholdson |
| 5,062,841 A | 11/1991 | Siegel |
| 5,084,749 A | 1/1992 | Losee et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,130,675 A | 7/1992 | Sugawara |
| 5,134,079 A | 7/1992 | Cusack et al. |
| 5,139,999 A | 8/1992 | Gordon et al. |
| 5,153,827 A | 10/1992 | Coutre et al. |
| 5,154,973 A | 10/1992 | Imagawa et al. |
| 5,165,406 A | 11/1992 | Wong |
| 5,176,662 A | 1/1993 | Bartholomew et al. |
| 5,178,609 A | 1/1993 | Ishikawa |
| 5,189,609 A | 2/1993 | Tivig et al. |
| 5,198,824 A | 3/1993 | Poradish |
| 5,205,819 A | 4/1993 | Ross et al. |
| 5,207,642 A | 5/1993 | Orkin et al. |
| 5,213,483 A | 5/1993 | Flaherty et al. |
| 5,217,754 A | 6/1993 | Santiago-Aviles et al. |
| 5,219,377 A | 6/1993 | Poradish |
| 5,232,439 A | 8/1993 | Campbell et al. |
| 5,237,993 A | 8/1993 | Skrabal |
| 5,239,326 A | 8/1993 | Takai |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,261,882 A | 11/1993 | Sealfon |
| 5,263,198 A | 11/1993 | Geddes et al. |
| 5,272,485 A | 12/1993 | Mason et al. |
| 5,273,517 A | 12/1993 | Barone et al. |
| 5,281,202 A | 1/1994 | Weber et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,346,476 A | 9/1994 | Elson |
| 5,364,342 A | 11/1994 | Beuchat et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,403,797 A | 4/1995 | Ohtani et al. |
| 5,411,889 A | 5/1995 | Hoots et al. |
| 5,421,812 A | 6/1995 | Langley et al. |
| 5,427,988 A | 6/1995 | Sengupta et al. |
| 5,433,710 A | 7/1995 | VanAntwerp et al. |
| 5,452,033 A | 9/1995 | Balling et al. |
| 5,456,945 A | 10/1995 | McMillan et al. |
| 5,468,727 A | 11/1995 | Phillips et al. |
| 5,478,610 A | 12/1995 | Desu et al. |
| 5,505,709 A | 4/1996 | Funderburk et al. |
| 5,505,828 A | 4/1996 | Wong et al. |
| 5,507,288 A | 4/1996 | Bocker et al. |
| 5,513,382 A | 4/1996 | Agahi-Kesheh et al. |
| 5,533,389 A | 7/1996 | Kamen et al. |
| 5,535,445 A | 7/1996 | Gunton |
| 5,540,772 A | 7/1996 | McMillan et al. |
| 5,543,773 A | 8/1996 | Evans et al. |
| 5,558,640 A | 9/1996 | Pfeiler et al. |
| 5,563,584 A | 10/1996 | Rader et al. |
| 5,569,186 A | 10/1996 | Lord et al. |

(56) References Cited

U.S. PATENT DOCUMENTS

| | | | |
|---|---|---|---|
| 5,576,781 A | 11/1996 | Deleeuw |
| 5,582,593 A | 12/1996 | Hultman |
| 5,584,053 A | 12/1996 | Kommrusch et al. |
| 5,584,813 A | 12/1996 | Livingston et al. |
| 5,585,733 A | 12/1996 | Paglione |
| 5,586,553 A | 12/1996 | Halili et al. |
| 5,590,387 A | 12/1996 | Schmidt et al. |
| 5,609,572 A | 3/1997 | Lang |
| 5,614,252 A | 3/1997 | McMillan et al. |
| 5,625,365 A | 4/1997 | Tom et al. |
| 5,635,433 A | 6/1997 | Sengupta |
| 5,637,095 A | 6/1997 | Nason et al. |
| 5,647,853 A | 7/1997 | Feldmann et al. |
| 5,660,163 A | 8/1997 | Schulman et al. |
| 5,665,065 A | 9/1997 | Colman et al. |
| 5,665,070 A | 9/1997 | McPhee |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,707,459 A | 1/1998 | Itoyama et al. |
| 5,707,715 A | 1/1998 | deRochemont et al. |
| 5,713,875 A | 2/1998 | Tanner, II |
| 5,714,123 A | 2/1998 | Sohrab |
| 5,716,343 A | 2/1998 | Kriesel et al. |
| 5,722,397 A | 3/1998 | Eppstein |
| 5,726,404 A | 3/1998 | Brody |
| 5,726,751 A | 3/1998 | Altendorf et al. |
| 5,741,228 A | 4/1998 | Lambrecht et al. |
| 5,746,217 A | 5/1998 | Erickson et al. |
| 5,747,350 A | 5/1998 | Sattler |
| 5,747,870 A | 5/1998 | Pedder |
| 5,748,827 A | 5/1998 | Holl et al. |
| 5,755,682 A | 5/1998 | Knudson et al. |
| 5,758,643 A | 6/1998 | Wong et al. |
| 5,759,923 A | 6/1998 | McMillan et al. |
| 5,764,189 A | 6/1998 | Lohninger |
| 5,771,567 A | 6/1998 | Pierce et al. |
| 5,776,103 A | 7/1998 | Kriesel et al. |
| 5,779,676 A | 7/1998 | Kriesel et al. |
| 5,785,681 A | 7/1998 | Indravudh et al. |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,807,075 A | 9/1998 | Jacobsen et al. |
| 5,817,007 A | 10/1998 | Fodgaard et al. |
| 5,820,622 A | 10/1998 | Gross et al. |
| 5,823,951 A | 10/1998 | Messerschmidt |
| 5,830,999 A | 11/1998 | Dunn |
| 5,839,467 A | 11/1998 | Saaski et al. |
| 5,840,020 A | 11/1998 | Heinonen et al. |
| 5,848,991 A | 12/1998 | Gross et al. |
| 5,851,197 A | 12/1998 | Marano et al. |
| 5,854,608 A | 12/1998 | Leisten |
| 5,858,005 A | 1/1999 | Kriesel |
| 5,858,239 A | 1/1999 | Kenley et al. |
| 5,859,621 A | 1/1999 | Leisten |
| 5,865,806 A | 2/1999 | Howell |
| 5,867,688 A | 2/1999 | Simmon et al. |
| 5,871,470 A | 2/1999 | McWha |
| 5,879,310 A | 3/1999 | Sopp et al. |
| 5,889,459 A | 3/1999 | Hattori et al. |
| 5,891,097 A | 4/1999 | Saito et al. |
| 5,892,489 A | 4/1999 | Kanba et al. |
| 5,897,530 A | 4/1999 | Jackson |
| 5,899,882 A | 5/1999 | Waksman et al. |
| 5,902,253 A | 5/1999 | Pfeiffer et al. |
| 5,903,421 A | 5/1999 | Furutani et al. |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,932,175 A | 8/1999 | Knute et al. |
| 5,933,121 A | 8/1999 | Rainhart et al. |
| 5,935,099 A | 8/1999 | Peterson et al. |
| 5,945,963 A | 8/1999 | Leisten |
| 5,947,911 A | 9/1999 | Wong et al. |
| 5,957,890 A | 9/1999 | Mann et al. |
| 5,961,492 A | 10/1999 | Kriesel et al. |
| 5,965,848 A | 10/1999 | Altschul et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,019,747 A | 2/2000 | McPhee |
| 6,023,251 A | 2/2000 | Koo et al. |
| 6,024,539 A | 2/2000 | Blomquist |
| 6,027,826 A | 2/2000 | deRochemont et al. |
| 6,028,568 A | 2/2000 | Asakura et al. |
| 6,031,445 A | 2/2000 | Marty et al. |
| 6,032,059 A | 2/2000 | Henning et al. |
| 6,036,924 A | 3/2000 | Simons et al. |
| 6,040,578 A | 3/2000 | Malin et al. |
| 6,040,805 A | 3/2000 | Huynh et al. |
| 6,046,707 A | 4/2000 | Gaughan et al. |
| 6,049,727 A | 4/2000 | Crothall |
| 6,050,978 A | 4/2000 | Orr et al. |
| 6,052,040 A | 4/2000 | Hino |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,111,544 A | 8/2000 | Dakeya et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,143,432 A | 11/2000 | de Rochemont et al. |
| 6,154,176 A | 11/2000 | Fathy et al. |
| 6,157,041 A | 12/2000 | Thomas et al. |
| 6,161,028 A | 12/2000 | Braig et al. |
| 6,162,639 A | 12/2000 | Douglas |
| 6,171,264 B1 | 1/2001 | Bader |
| 6,174,300 B1 | 1/2001 | Kriesel et al. |
| 6,176,004 B1 | 1/2001 | Rainhart et al. |
| 6,181,297 B1 | 1/2001 | Leisten |
| 6,188,368 B1 | 2/2001 | Koriyama et al. |
| 6,190,359 B1 | 2/2001 | Heruth |
| 6,195,049 B1 | 2/2001 | Kim et al. |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,204,203 B1 | 3/2001 | Narwankar et al. |
| 6,208,843 B1 | 3/2001 | Huang et al. |
| 6,214,629 B1 | 4/2001 | Freitag et al. |
| 6,222,489 B1 | 4/2001 | Tsuru et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,266,020 B1 | 7/2001 | Chang |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,300,894 B1 | 10/2001 | Lynch et al. |
| 6,309,370 B1 | 10/2001 | Haim et al. |
| 6,312,888 B1 | 11/2001 | Wong et al. |
| 6,320,547 B1 | 11/2001 | Fathy et al. |

(56)                    References Cited

U.S. PATENT DOCUMENTS

| | | |
|---|---|---|
| 6,323,549 B1 | 11/2001 | deRochemont et al. |
| 6,334,851 B1 | 1/2002 | Hayes et al. |
| 6,363,609 B1 | 4/2002 | Pickren |
| 6,375,627 B1 | 4/2002 | Mauze et al. |
| 6,375,638 B2 | 4/2002 | Nason et al. |
| 6,379,301 B1 | 4/2002 | Worthington et al. |
| 6,381,029 B1 | 4/2002 | Tipirneni |
| 6,399,745 B1 * | 6/2002 | Ertl ........................... A61P 3/10 |
| | | 530/350 |
| 6,402,689 B1 | 6/2002 | Scarantino et al. |
| 6,468,242 B1 | 10/2002 | Wilson |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Viana et al. |
| 6,512,937 B2 | 1/2003 | Blank et al. |
| 6,520,936 B1 | 2/2003 | Mann |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,537,249 B2 | 3/2003 | Kriesell et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,546,268 B1 | 4/2003 | Ishikawa et al. |
| 6,546,269 B1 | 4/2003 | Kurnik |
| 6,552,693 B1 | 4/2003 | Leisten |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,583,699 B2 | 6/2003 | Yokoyama |
| 6,595,956 B1 | 7/2003 | Gross et al. |
| 6,605,151 B1 | 8/2003 | Wessels et al. |
| 6,611,419 B1 | 8/2003 | Chakravorty |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,642,908 B2 | 11/2003 | Pleva et al. |
| 6,645,142 B2 | 11/2003 | Braig et al. |
| 6,650,303 B2 | 11/2003 | Kim et al. |
| 6,653,091 B1 | 11/2003 | Dunn et al. |
| 6,656,158 B2 | 12/2003 | Mahoney et al. |
| 6,662,030 B2 | 12/2003 | Khalil et al. |
| 6,669,663 B1 | 12/2003 | Thompson |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,685,452 B2 | 2/2004 | Christiansen et al. |
| 6,686,406 B2 | 2/2004 | Tomomatsu et al. |
| 6,690,336 B1 | 2/2004 | Leisten et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,890 B2 | 5/2004 | Imanaka et al. |
| 6,740,059 B2 | 5/2004 | Flaherty |
| 6,740,072 B2 | 5/2004 | Starkweather et al. |
| 6,741,148 B2 | 5/2004 | Killen et al. |
| 6,742,249 B2 | 6/2004 | deRochemont et al. |
| 6,743,744 B1 | 6/2004 | Kim et al. |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,753,745 B2 | 6/2004 | Killen et al. |
| 6,753,814 B2 | 6/2004 | Killen et al. |
| 6,758,835 B2 | 7/2004 | Close et al. |
| 6,762,237 B2 | 7/2004 | Glatkowski et al. |
| 6,768,319 B2 | 7/2004 | Wang |
| 6,780,156 B2 | 8/2004 | Haueter et al. |
| 6,787,181 B2 | 9/2004 | Uchiyama et al. |
| 6,791,496 B1 | 9/2004 | Killen et al. |
| 6,810,290 B2 | 10/2004 | Lebel et al. |
| 6,826,031 B2 | 11/2004 | Nagai et al. |
| 6,830,558 B2 | 12/2004 | Flaherty et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,853,288 B2 | 2/2005 | Ahn et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,878,871 B2 | 4/2005 | Scher et al. |
| 6,883,778 B1 | 4/2005 | Newton et al. |
| 6,890,291 B2 | 5/2005 | Robinson et al. |
| 6,900,016 B1 * | 5/2005 | Venter ................... C07H 21/04 |
| | | 536/23.4 |
| 6,905,989 B2 | 6/2005 | Ellis et al. |
| 6,906,674 B2 | 6/2005 | McKinzie, III et al. |
| 6,914,566 B2 | 7/2005 | Beard |
| 6,919,119 B2 | 7/2005 | Kalkan et al. |
| 6,928,298 B2 | 8/2005 | Furutani et al. |
| 6,936,029 B2 | 8/2005 | Mann et al. |
| 6,943,430 B2 | 9/2005 | Kwon |
| 6,943,731 B2 | 9/2005 | Killen et al. |
| 6,949,081 B1 | 9/2005 | Chance |
| 6,958,809 B2 | 10/2005 | Sterling et al. |
| 6,963,259 B2 | 11/2005 | Killen et al. |
| 6,989,891 B2 | 1/2006 | Braig et al. |
| 6,990,366 B2 | 1/2006 | Say et al. |
| 7,002,436 B2 | 2/2006 | Ma et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,047,637 B2 | 5/2006 | deRochemont et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,137,694 B2 | 11/2006 | Ferran et al. |
| 7,139,593 B2 | 11/2006 | Kavak et al. |
| 7,139,598 B2 | 11/2006 | Hull et al. |

(56)                  References Cited

U.S. PATENT DOCUMENTS

| | | | |
|---|---|---|---|
| 7,144,384 | B2 | 12/2006 | Gorman et al. |
| 7,160,272 | B1 | 1/2007 | Eyal et al. |
| 7,171,252 | B1 | 1/2007 | Scarantino et al. |
| 7,182,726 | B2 | 2/2007 | Williams et al. |
| 7,190,988 | B2 | 3/2007 | Say et al. |
| 7,204,823 | B2 | 4/2007 | Estes et al. |
| 7,230,316 | B2 | 6/2007 | Yamazaki et al. |
| 7,248,912 | B2 | 7/2007 | Gough et al. |
| 7,267,665 | B2 | 9/2007 | Steil et al. |
| 7,271,912 | B2 | 9/2007 | Sterling et al. |
| 7,278,983 | B2 | 10/2007 | Ireland et al. |
| 7,291,107 | B2 | 11/2007 | Hellwig et al. |
| 7,291,497 | B2 | 11/2007 | Holmes et al. |
| 7,291,782 | B2 | 11/2007 | Sager et al. |
| 7,303,073 | B2 | 12/2007 | Raynal-Olive et al. |
| 7,303,549 | B2 | 12/2007 | Flaherty et al. |
| 7,303,622 | B2 | 12/2007 | Loch et al. |
| 7,303,922 | B2 | 12/2007 | Jeng et al. |
| 7,354,420 | B2 | 4/2008 | Steil et al. |
| 7,388,202 | B2 | 6/2008 | Sterling et al. |
| 7,402,153 | B2 | 7/2008 | Steil et al. |
| 7,404,796 | B2 | 7/2008 | Ginsberg |
| 7,405,698 | B2 | 7/2008 | de Rochemont |
| 7,429,255 | B2 | 9/2008 | Thompson |
| 7,460,130 | B2 | 12/2008 | Salganicoff |
| 7,481,787 | B2 | 1/2009 | Gable et al. |
| 7,491,187 | B2 | 2/2009 | Van Den Berghe et al. |
| 7,500,949 | B2 | 3/2009 | Gottlieb et al. |
| 7,509,156 | B2 | 3/2009 | Flanders |
| 7,522,124 | B2 | 4/2009 | Smith et al. |
| 7,547,281 | B2 | 6/2009 | Hayes et al. |
| 7,553,512 | B2 | 6/2009 | Kodas et al. |
| 7,564,887 | B2 | 7/2009 | Wang et al. |
| 7,569,030 | B2 | 8/2009 | Lebel et al. |
| 7,595,623 | B2 | 9/2009 | Bennett |
| 7,608,042 | B2 | 10/2009 | Goldberger et al. |
| 7,651,845 | B2 | 1/2010 | Doyle, III et al. |
| 7,652,901 | B2 | 1/2010 | Kirchmeier et al. |
| 7,680,529 | B2 | 3/2010 | Kroll |
| 7,714,794 | B2 | 5/2010 | Tavassoli Hozouri |
| 7,734,323 | B2 | 6/2010 | Blomquist et al. |
| 7,763,917 | B2 | 7/2010 | de Rochemont |
| 7,766,829 | B2 | 8/2010 | Sloan et al. |
| 7,771,391 | B2 | 8/2010 | Carter |
| 7,785,258 | B2 | 8/2010 | Braig et al. |
| 7,806,854 | B2 | 10/2010 | Damiano et al. |
| 7,806,886 | B2 | 10/2010 | Kanderian, Jr. et al. |
| 7,812,774 | B2 | 10/2010 | Friman et al. |
| 7,918,825 | B2 | 4/2011 | OConnor et al. |
| 7,946,985 | B2 | 5/2011 | Mastrototaro et al. |
| 7,972,296 | B2 | 7/2011 | Braig et al. |
| 8,056,719 | B2 | 11/2011 | Porret et al. |
| 8,066,805 | B2 | 11/2011 | Zurcher et al. |
| 8,069,690 | B2 | 12/2011 | DeSantolo et al. |
| 8,105,282 | B2 | 1/2012 | Susi et al. |
| 8,114,489 | B2 | 2/2012 | Nemat-Nasser et al. |
| 8,178,457 | B2 | 5/2012 | De Rochemont |
| 8,193,873 | B2 | 6/2012 | Kato et al. |
| 8,221,345 | B2 | 7/2012 | Blomquist |
| 8,251,907 | B2 | 8/2012 | Sterling et al. |
| 8,267,921 | B2 | 9/2012 | Yodfat et al. |
| 8,285,487 | B2 | 10/2012 | Bergstrom et al. |
| 8,350,657 | B2 | 1/2013 | deRochemont |
| 8,354,294 | B2 | 1/2013 | de Rochemont et al. |
| 8,449,524 | B2 | 5/2013 | Braig et al. |
| 8,452,359 | B2 | 5/2013 | Rebec et al. |
| 8,454,557 | B1 | 6/2013 | Qi et al. |
| 8,454,576 | B2 | 6/2013 | Mastrototaro et al. |
| 8,461,561 | B2 | 6/2013 | Freeman et al. |
| 8,467,980 | B2 | 6/2013 | Campbell et al. |
| 8,478,557 | B2 | 7/2013 | Hayter et al. |
| 8,547,239 | B2 | 10/2013 | Peatfield et al. |
| 8,593,819 | B2 | 11/2013 | de Rochemont |
| 8,597,274 | B2 | 12/2013 | Sloan et al. |
| 8,622,954 | B2 | 1/2014 | Shahmirian |

| | | | | |
|---|---|---|---|---|
| 8,622,988 | B2 | 1/2014 | Hayter | |
| 8,715,839 | B2 | 5/2014 | de Rochemont | |
| 8,727,117 | B2 | 5/2014 | Maasarani | |
| 8,810,394 | B2 | 8/2014 | Kalpin | |
| 8,818,782 | B2 | 8/2014 | Thukral et al. | |
| 8,920,628 | B2 * | 12/2014 | Gerber | A61B 5/14532 |
| | | | | 205/792 |
| 8,939,935 | B2 | 1/2015 | OConnor et al. | |
| 9,005,166 | B2 | 4/2015 | Uber, III et al. | |
| 9,061,097 | B2 | 6/2015 | Holt et al. | |
| 9,171,343 | B1 | 10/2015 | Fischell et al. | |
| 9,180,244 | B2 | 11/2015 | Anderson et al. | |
| 9,192,716 | B2 | 11/2015 | Jugl et al. | |
| 9,233,204 | B2 | 1/2016 | Booth et al. | |
| 9,248,229 | B2 | 2/2016 | Devouassoux et al. | |
| 9,402,950 | B2 | 8/2016 | Dilanni et al. | |
| 9,427,710 | B2 | 8/2016 | Jansen | |
| 9,486,571 | B2 | 11/2016 | Rosinko | |
| 9,520,649 | B2 | 12/2016 | de Rochemont | |
| 9,579,456 | B2 | 2/2017 | Budiman et al. | |
| 9,598,195 | B2 | 3/2017 | Deutschle et al. | |
| 9,656,017 | B2 | 5/2017 | Greene | |
| 9,743,224 | B2 | 8/2017 | San Vicente et al. | |
| 9,857,090 | B2 | 1/2018 | Golden et al. | |
| 9,862,519 | B2 | 1/2018 | Deutschle et al. | |
| 9,907,515 | B2 | 3/2018 | Doyle, III et al. | |
| 9,974,903 | B1 | 5/2018 | Davis et al. | |
| 9,980,140 | B1 | 5/2018 | Spencer et al. | |
| 9,984,773 | B2 | 5/2018 | Gondhalekar et al. | |
| 10,046,114 | B1 | 8/2018 | Biederman et al. | |
| 10,080,840 | B2 | 9/2018 | Gescheit et al. | |
| 10,086,131 | B2 | 10/2018 | Okihara | |
| 10,248,839 | B2 | 4/2019 | Levy et al. | |
| 10,335,464 | B1 | 7/2019 | Michelich et al. | |
| 10,342,926 | B2 | 7/2019 | Nazzaro et al. | |
| 10,441,717 | B2 | 10/2019 | Schmid et al. | |
| 10,583,250 | B2 | 3/2020 | Mazlish et al. | |
| 10,736,548 | B2 | 8/2020 | Ahmad et al. | |
| 10,737,024 | B2 | 8/2020 | Schmid | |
| 10,987,468 | B2 | 4/2021 | Mazlish et al. | |
| 11,197,964 | B2 | 12/2021 | Sjolund et al. | |
| 11,260,169 | B2 | 3/2022 | Estes | |
| 11,538,587 | B2 * | 12/2022 | Bill | G16H 20/60 |
| 12,226,239 | B2 * | 2/2025 | Williams | A61B 5/4848 |
| 2001/0021803 | A1 | 9/2001 | Blank et al. | |
| 2001/0034023 | A1 | 10/2001 | Stanton, Jr. et al. | |
| 2001/0034502 | A1 | 10/2001 | Moberg et al. | |
| 2001/0048969 | A1 | 12/2001 | Constantino et al. | |
| 2001/0051377 | A1 | 12/2001 | Hammer et al. | |
| 2001/0053895 | A1 | 12/2001 | Vaillancourt | |
| 2001/0056258 | A1 | 12/2001 | Evans | |
| 2002/0010401 | A1 | 1/2002 | Bushmakin et al. | |
| 2002/0010423 | A1 | 1/2002 | Gross et al. | |
| 2002/0016568 | A1 | 2/2002 | Lebel et al. | |
| 2002/0032374 | A1 | 3/2002 | Holker et al. | |
| 2002/0040208 | A1 | 4/2002 | Flaherty et al. | |
| 2002/0047768 | A1 | 4/2002 | Duffy | |
| 2002/0070983 | A1 | 6/2002 | Kozub et al. | |
| 2002/0123740 | A1 | 9/2002 | Flaherty et al. | |
| 2002/0128543 | A1 | 9/2002 | Leonhardt | |
| 2002/0147423 | A1 | 10/2002 | Burbank et al. | |
| 2002/0155425 | A1 | 10/2002 | Han et al. | |
| 2002/0161288 | A1 | 10/2002 | Shin et al. | |
| 2002/0161307 | A1 | 10/2002 | Yu et al. | |
| 2002/0173769 | A1 | 11/2002 | Gray et al. | |
| 2002/0190818 | A1 | 12/2002 | Endou et al. | |
| 2003/0023148 | A1 | 1/2003 | Lorenz et al. | |
| 2003/0034124 | A1 | 2/2003 | Sugaya et al. | |
| 2003/0040715 | A1 | 2/2003 | DAntonio et al. | |
| 2003/0050621 | A1 | 3/2003 | Lebel et al. | |
| 2003/0060692 | A1 | 3/2003 | Ruchti et al. | |
| 2003/0073952 | A1 | 4/2003 | Flaherty et al. | |
| 2003/0086074 | A1 | 5/2003 | Braig et al. | |
| 2003/0086075 | A1 | 5/2003 | Braig et al. | |
| 2003/0090649 | A1 | 5/2003 | Sterling et al. | |
| 2003/0100040 | A1 | 5/2003 | Bonnecaze et al. | |
| 2003/0122647 | A1 | 7/2003 | Ou | |
| 2003/0130616 | A1 | 7/2003 | Steil et al. | |
| 2003/0135388 | A1 | 7/2003 | Martucci et al. | |

(56) References Cited

U.S. PATENT DOCUMENTS

| | | |
|---|---|---|
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0163789 A1 | 8/2003 | Blomquist |
| 2003/0170436 A1 | 9/2003 | Sumi et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2003/0221621 A1 | 12/2003 | Pokharna et al. |
| 2004/0010207 A1 | 1/2004 | Flaherty et al. |
| 2004/0010507 A1 | 1/2004 | Bellew |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064259 A1 | 4/2004 | Haaland et al. |
| 2004/0068224 A1 | 4/2004 | Couvillon, Jr. et al. |
| 2004/0069044 A1 | 4/2004 | Lavi et al. |
| 2004/0085215 A1 | 5/2004 | Moberg et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Noue et al. |
| 2005/0022274 A1 | 1/2005 | Campbell |
| 2005/0033148 A1 | 2/2005 | Haueter et al. |
| 2005/0038680 A1 | 2/2005 | McMahon |
| 2005/0049179 A1 | 3/2005 | Davidson et al. |
| 2005/0055242 A1 | 3/2005 | Bello et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0134609 A1 | 6/2005 | Yu |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0262451 A1 | 11/2005 | Remignanti et al. |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0041229 A1 | 2/2006 | Garibotto et al. |
| 2006/0079765 A1 | 4/2006 | Neer et al. |
| 2006/0079809 A1 | 4/2006 | Goldberger et al. |
| 2006/0086909 A1 | 4/2006 | Schaber |
| 2006/0086994 A1 | 4/2006 | Viefers et al. |
| 2006/0092569 A1 | 5/2006 | Che et al. |
| 2006/0100494 A1 | 5/2006 | Kroll |
| 2006/0134323 A1 | 6/2006 | OBrien |
| 2006/0134491 A1 | 6/2006 | Hilchenko et al. |
| 2006/0167350 A1 | 7/2006 | Monfre et al. |
| 2006/0173406 A1 | 8/2006 | Hayes et al. |
| 2006/0178633 A1 | 8/2006 | Garibotto et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0264926 A1 | 11/2006 | Kochamba |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0027370 A1 | 2/2007 | Brauker et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0078784 A1 | 4/2007 | Donovan et al. |
| 2007/0083160 A1 | 4/2007 | Hall et al. |
| 2007/0100635 A1 | 5/2007 | Mahajan et al. |
| 2007/0106135 A1 | 5/2007 | Sloan et al. |
| 2007/0112298 A1 | 5/2007 | Mueller et al. |
| 2007/0116601 A1 | 5/2007 | Patton |
| 2007/0118405 A1 | 5/2007 | Campbell |
| 2007/0129690 A1 | 6/2007 | Rosenblatt et al. |
| 2007/0142720 A1 | 6/2007 | Ridder et al. |
| 2007/0166453 A1 | 7/2007 | Van Duren et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0179885 A1 | 8/2007 | Bird et al. |
| 2007/0191702 A1 | 8/2007 | Yodfat |
| 2007/0191716 A1 | 8/2007 | Goldberger et al. |
| 2007/0191770 A1 | 8/2007 | Moberg et al. |
| 2007/0197163 A1 | 8/2007 | Robertson |
| 2007/0225675 A1 | 9/2007 | Robinson et al. |
| 2007/0233051 A1 | 10/2007 | Hohl et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0004515 A1 | 1/2008 | Jennewine |
| 2008/0027371 A1 | 1/2008 | Higuchi et al. |
| 2008/0033272 A1 | 2/2008 | Gough et al. |
| 2008/0051738 A1 | 2/2008 | Griffin |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0077081 A1 | 3/2008 | Mounce et al. |
| 2008/0078400 A1 | 4/2008 | Martens et al. |
| 2008/0097289 A1 | 4/2008 | Steil et al. |
| 2008/0114304 A1 | 5/2008 | Nalesso et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |
| 2008/0172026 A1 | 7/2008 | Blomquist |
| 2008/0172028 A1 | 7/2008 | Blomquist |
| 2008/0172031 A1 | 7/2008 | Blomquist |
| 2008/0173073 A1 | 7/2008 | Downie et al. |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0255438 A1 | 10/2008 | Saidara et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0281290 A1 | 11/2008 | Yodfat et al. |
| 2008/0287906 A1 | 11/2008 | Burkholz et al. |
| 2009/0006061 A1 | 1/2009 | Thukral et al. |
| 2009/0018406 A1 | 1/2009 | Yodfat |
| 2009/0030398 A1 | 1/2009 | Yodfat |

(56)         References Cited

U.S. PATENT DOCUMENTS

| | | |
|---|---|---|
| 2009/0036753 A1 | 2/2009 | King |
| 2009/0043240 A1 | 2/2009 | Robinson et al. |
| 2009/0048556 A1 | 2/2009 | Durand |
| 2009/0054753 A1 | 2/2009 | Robinson et al. |
| 2009/0062767 A1 | 3/2009 | Van Antwerp et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0112769 A1 | 4/2009 | Dicks et al. |
| 2009/0131861 A1 | 5/2009 | Braig et al. |
| 2009/0143661 A1 | 6/2009 | Taub |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0177142 A1 | 7/2009 | Blomquist et al. |
| 2009/0177147 A1 | 7/2009 | Blomquist |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0254041 A1 | 10/2009 | Krag et al. |
| 2009/0318791 A1 | 12/2009 | Kaastrup |
| 2009/0326343 A1 | 12/2009 | Gable et al. |
| 2009/0326472 A1 | 12/2009 | Carter |
| 2010/0017141 A1 | 1/2010 | Campbell et al. |
| 2010/0036326 A1 | 2/2010 | Matusch |
| 2010/0057042 A1 | 3/2010 | Hayter |
| 2010/0064243 A1 | 3/2010 | Buck et al. |
| 2010/0076275 A1 | 3/2010 | Chu et al. |
| 2010/0077198 A1 | 3/2010 | Buck et al. |
| 2010/0094251 A1 | 4/2010 | Estes |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0174228 A1 | 7/2010 | Buckingham et al. |
| 2010/0185175 A1 | 7/2010 | Kamen |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0262117 A1 | 10/2010 | Magni et al. |
| 2010/0262434 A1 | 10/2010 | Shaya |
| 2010/0286997 A1 | 11/2010 | Srinivasan |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0049394 A1 | 3/2011 | de Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0124996 A1 | 5/2011 | Reinke et al. |
| 2011/0142688 A1 | 6/2011 | Chappel et al. |
| 2011/0144586 A1 | 6/2011 | Michaud et al. |
| 2011/0152658 A1 | 6/2011 | Peyser et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0213306 A1 | 9/2011 | Hanson et al. |
| 2011/0218495 A1 | 9/2011 | Remebe |
| 2011/0225024 A1 | 9/2011 | Seyer et al. |
| 2011/0230833 A1 | 9/2011 | Landman et al. |
| 2011/0246235 A1 | 10/2011 | Powell et al. |
| 2011/0251509 A1 | 10/2011 | Beyhan et al. |
| 2011/0257496 A1 | 10/2011 | Terashima |
| 2011/0313680 A1 | 12/2011 | Doyle, III |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0029941 A1 | 2/2012 | Malave et al. |
| 2012/0030393 A1 | 2/2012 | Ganesh et al. |
| 2012/0050046 A1 | 3/2012 | Satorius et al. |
| 2012/0053556 A1 | 3/2012 | Lee |
| 2012/0054841 A1 | 3/2012 | Schultz et al. |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0153936 A1 | 6/2012 | Romani et al. |
| 2012/0172833 A1 | 7/2012 | Zisapel |
| 2012/0182939 A1 | 7/2012 | Rajan et al. |
| 2012/0184909 A1 | 7/2012 | Gyrn |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0219935 A1 | 8/2012 | Stebbings |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0250449 A1 | 10/2012 | Nakano |
| 2012/0265166 A1 | 10/2012 | Yodfat |
| 2012/0271655 A1 | 10/2012 | Knobel et al. |
| 2012/0277667 A1 | 11/2012 | Yodat et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0030841 A1 | 1/2013 | Bergstrom et al. |
| 2013/0036100 A1 | 2/2013 | Nagpal et al. |
| 2013/0060194 A1 | 3/2013 | Rostein |
| 2013/0080832 A1 | 3/2013 | Dean et al. |
| 2013/0138452 A1 | 5/2013 | Cork et al. |
| 2013/0158503 A1 | 6/2013 | Kanderian, Jr. et al. |
| 2013/0172695 A1 | 7/2013 | Nielsen et al. |
| 2013/0172710 A1 | 7/2013 | Mears et al. |
| 2013/0173473 A1 | 7/2013 | Birtwhistle et al. |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0253472 A1 | 9/2013 | Cabiri |
| 2013/0261406 A1 | 10/2013 | Rebec et al. |
| 2013/0274576 A1 | 10/2013 | Amirouche et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | OConnor et al. |
| 2013/0346858 A1 | 12/2013 | Neyrinck |
| 2014/0005633 A1 | 1/2014 | Finan |
| 2014/0018730 A1 | 1/2014 | Muller-Pathle |
| 2014/0032549 A1 | 1/2014 | McDaniel et al. |
| 2014/0066886 A1 | 3/2014 | Roy et al. |
| 2014/0066887 A1 | 3/2014 | Mastrototaro et al. |
| 2014/0074033 A1 | 3/2014 | Sonderegger et al. |
| 2014/0074059 A1 | 3/2014 | Howell |
| 2014/0088428 A1 | 3/2014 | Yang et al. |
| 2014/0108046 A1 | 4/2014 | Cabrera et al. |
| 2014/0114277 A1 | 4/2014 | Eggert et al. |
| 2014/0121635 A1 | 5/2014 | Hayter |
| 2014/0128839 A1 | 5/2014 | Dilanni et al. |
| 2014/0129951 A1 | 5/2014 | Amin et al. |
| 2014/0135880 A1 | 5/2014 | Baumgartner et al. |
| 2014/0142508 A1 | 5/2014 | Dilanni et al. |
| 2014/0146202 A1 | 5/2014 | Boss et al. |
| 2014/0163664 A1 | 6/2014 | Goldsmith |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |

(56) References Cited

U.S. PATENT DOCUMENTS

| | | |
|---|---|---|
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025503 A1 | 1/2015 | Searle et al. |
| 2015/0038898 A1 | 2/2015 | Palmer et al. |
| 2015/0041498 A1 | 2/2015 | Kakiuchi et al. |
| 2015/0057913 A1 | 2/2015 | Benhammou |
| 2015/0119666 A1 | 4/2015 | Brister et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0151050 A1 | 6/2015 | Estes |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217046 A1 | 8/2015 | Heller |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0290391 A1 | 10/2015 | Schmid et al. |
| 2015/0301691 A1 | 10/2015 | Qin |
| 2015/0306314 A1 | 10/2015 | Doyle et al. |
| 2015/0331995 A1 | 11/2015 | Zhao et al. |
| 2015/0351671 A1 | 12/2015 | Vanslyke et al. |
| 2015/0352280 A1 | 12/2015 | Deratany |
| 2015/0356250 A1 | 12/2015 | Polimeni |
| 2015/0366945 A1 | 12/2015 | Greene et al. |
| 2016/0015891 A1 | 1/2016 | Papiorek |
| 2016/0019352 A1 | 1/2016 | Cohen et al. |
| 2016/0022905 A1 | 1/2016 | Nagar et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0184517 A1 | 6/2016 | Baek et al. |
| 2016/0220181 A1 | 8/2016 | Rigooard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0339172 A1 | 11/2016 | Michaud et al. |
| 2016/0354543 A1 | 12/2016 | Cinar et al. |
| 2017/0021096 A1 | 1/2017 | Cole et al. |
| 2017/0049386 A1 | 2/2017 | Abraham et al. |
| 2017/0053552 A1 | 2/2017 | Zhong |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0189625 A1 | 7/2017 | Cirillo et al. |
| 2017/0213002 A1 | 7/2017 | Jha |
| 2017/0216524 A1 | 8/2017 | Haider et al. |
| 2017/0239415 A1 | 8/2017 | Hwang et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0332951 A1* | 11/2017 | Ahmad .................. G16H 50/20 |
| 2017/0348482 A1 | 12/2017 | Duke et al. |
| 2018/0014113 A1* | 1/2018 | Boesen ................ A61B 5/4866 |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277246 A1* | 9/2018 | Zhong .................. G06F 16/288 |
| 2018/0277253 A1 | 9/2018 | Gondhalekar et al. |
| 2018/0280609 A1 | 10/2018 | Nishimura et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De Wever et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0101286 A1* | 4/2020 | Windmiller .......... A61B 5/1468 |
| 2020/0113515 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2021/0225480 A1 | 7/2021 | Desborough |
| 2022/0023536 A1 | 1/2022 | Graham et al. |
| 2022/0273872 A1 | 9/2022 | Narayanaswami |
| 2023/0128193 A1* | 4/2023 | Williams ............. A61B 5/7455 |
| | | 715/711 |
| 2023/0338652 A1* | 10/2023 | Narayanaswami .... G16H 20/17 |
| 2023/0343430 A1* | 10/2023 | Narayanaswami .... G16H 20/30 |
| 2024/0099612 A1* | 3/2024 | Budiman ........... A61B 5/14532 |
| 2024/0206772 A1* | 6/2024 | Hayter ................... A61B 5/746 |
| 2024/0306949 A1* | 9/2024 | Kumar ................. A61B 5/7275 |
| 2025/0255560 A1* | 8/2025 | Williams ............. A61B 5/4857 |

FOREIGN PATENT DOCUMENTS

| | | |
|---|---|---|
| CA | 2863379 A1 | 8/2013 |
| CN | 1297140 A | 5/2001 |
| CN | 101208699 A | 6/2008 |
| CN | 201134101 Y | 10/2008 |
| DE | 4200595 A1 | 7/1993 |
| DE | 19756872 A1 | 7/1999 |
| EP | 0026056 A1 | 4/1981 |
| EP | 0341049 A2 | 11/1989 |
| EP | 0496305 A2 | 7/1992 |
| EP | 0549341 A1 | 6/1993 |
| EP | 0867196 A2 | 9/1998 |
| EP | 0939451 A1 | 9/1999 |
| EP | 1177802 A1 | 2/2002 |
| EP | 1376759 A2 | 1/2004 |
| EP | 1491144 A1 | 12/2004 |
| EP | 0801578 B1 | 7/2006 |
| EP | 1762263 A1 | 3/2007 |
| EP | 1839694 A1 | 10/2007 |
| EP | 1852703 A1 | 11/2007 |
| EP | 2099384 A1 | 9/2009 |
| EP | 2139382 A1 | 1/2010 |
| EP | 2353628 A2 | 8/2011 |
| EP | 2397181 A1 | 12/2011 |
| EP | 2468338 A1 | 6/2012 |

(56)        References Cited

FOREIGN PATENT DOCUMENTS

| | | | |
|---|---|---|---|
| EP | 2666520 | A1 | 11/2013 |
| EP | 2695573 | A2 | 2/2014 |
| EP | 2703024 | A1 | 3/2014 |
| EP | 1874390 | B1 | 10/2014 |
| EP | 2830499 | A1 | 2/2015 |
| EP | 2943149 | A1 | 11/2015 |
| EP | 3068290 | A1 | 9/2016 |
| EP | 3177344 | A1 | 6/2017 |
| EP | 3187201 | A1 | 7/2017 |
| EP | 3193979 | A1 | 7/2017 |
| EP | 3314548 | A1 | 5/2018 |
| EP | 1571582 | B1 | 4/2019 |
| EP | 2897071 | B1 | 5/2019 |
| EP | 3598942 | A1 | 1/2020 |
| EP | 3607985 | A1 | 2/2020 |
| ES | 2559866 | T3 | 2/2016 |
| FR | 2096275 | A5 | 2/1972 |
| GB | 1125897 | A | 9/1968 |
| GB | 1401588 | A | 7/1975 |
| GB | 2176595 | A | 12/1986 |
| GB | 2443260 | A | 4/2008 |
| GB | 2443261 | A | 4/2008 |
| GB | 2461086 | A | 12/2009 |
| GB | 2495014 | A | 3/2013 |
| GB | 2524717 | A | 10/2015 |
| GB | 2525149 | A | 10/2015 |
| JP | 51125993 | A | 11/1976 |
| JP | 02131777 | A | 5/1990 |
| JP | 2001190659 | A | 7/2001 |
| JP | 2003154190 | A | 5/2003 |
| JP | 2005326943 | A | 11/2005 |
| JP | 2007144141 | A1 | 6/2007 |
| JP | 2004283378 | A | 10/2007 |
| JP | 2007307359 | A | 11/2007 |
| JP | 2008513142 | A | 5/2008 |
| JP | 2008242502 | A | 10/2008 |
| JP | 2012210441 | A | 11/2012 |
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 200048112 | A2 | 9/1968 |
| WO | 8606796 | A1 | 11/1986 |
| WO | 9800193 | A1 | 1/1998 |
| WO | 9801071 | A1 | 1/1998 |
| WO | 9819145 | A1 | 5/1998 |
| WO | 9824495 | A1 | 6/1998 |
| WO | 9841267 | A1 | 9/1998 |
| WO | 9855073 | A1 | 12/1998 |
| WO | 9910040 | A1 | 3/1999 |
| WO | 9910049 | A1 | 3/1999 |
| WO | 9956803 | A1 | 11/1999 |
| WO | 9962576 | A1 | 12/1999 |
| WO | 0010628 | A2 | 3/2000 |
| WO | 0013580 | A1 | 3/2000 |
| WO | 0019887 | A1 | 4/2000 |
| WO | 0030705 | A1 | 6/2000 |
| WO | 200032258 | A1 | 6/2000 |
| WO | 0061215 | A1 | 10/2000 |
| WO | 0078210 | A1 | 12/2000 |
| WO | 0172354 | A2 | 10/2001 |
| WO | 2001078812 | A1 | 10/2001 |
| WO | 2002015954 | A1 | 2/2002 |
| WO | 0226282 | A2 | 4/2002 |
| WO | 2002043866 | A2 | 6/2002 |
| WO | 2002076535 | A1 | 10/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2003097133 | A1 | 11/2003 |
| WO | 2004043250 | A1 | 5/2004 |
| WO | 2005110601 | A1 | 5/2004 |
| WO | 2004092715 | A1 | 10/2004 |
| WO | 2005031631 | A2 | 4/2005 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2006060668 | A2 | 6/2006 |
| WO | 2007064835 | A2 | 6/2007 |
| WO | 2007066152 | A2 | 6/2007 |
| WO | 2007078937 | A1 | 7/2007 |
| WO | 2007112034 | A2 | 10/2007 |
| WO | 2008024810 | A2 | 2/2008 |
| WO | 2008024814 | A2 | 2/2008 |
| WO | 2008029403 | A1 | 3/2008 |
| WO | 2008133702 | A1 | 11/2008 |
| WO | 2009023634 | A2 | 2/2009 |
| WO | 2009032399 | A1 | 3/2009 |
| WO | 2009039203 | A2 | 3/2009 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010022069 | A2 | 2/2010 |
| WO | 2010025433 | A1 | 3/2010 |
| WO | 2010053702 | A1 | 5/2010 |
| WO | 2010077279 | A1 | 7/2010 |
| WO | 2010078434 | A2 | 7/2010 |
| WO | 2010132077 | A1 | 11/2010 |
| WO | 2010138848 | A1 | 12/2010 |
| WO | 2010139793 | A1 | 12/2010 |
| WO | 2010146579 | A1 | 12/2010 |
| WO | 2010147659 | A2 | 12/2010 |
| WO | 2011012465 | A1 | 2/2011 |
| WO | 2011031458 | A1 | 3/2011 |
| WO | 2011075042 | A1 | 6/2011 |
| WO | 2011095483 | A1 | 8/2011 |
| WO | 2011133823 | A1 | 10/2011 |
| WO | 2012045667 | A2 | 4/2012 |
| WO | 2012073032 | A1 | 6/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013050535 | A2 | 4/2013 |
| WO | 2013078200 | A1 | 5/2013 |
| WO | 2013134486 | A2 | 9/2013 |
| WO | 2013149186 | A1 | 10/2013 |
| WO | 20130149186 | A1 | 10/2013 |
| WO | 2013177565 | A1 | 11/2013 |
| WO | 2013182321 | A1 | 12/2013 |
| WO | 2014029416 | A1 | 2/2014 |
| WO | 2014109898 | A1 | 7/2014 |
| WO | 2014110538 | A1 | 7/2014 |
| WO | 2014136105 | A1 | 9/2014 |
| WO | 2014149357 | A1 | 9/2014 |
| WO | 2014179774 | A1 | 11/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015117082 | A1 | 8/2015 |
| WO | 2015117854 | A1 | 8/2015 |
| WO | 2015167201 | A1 | 11/2015 |
| WO | 2015177082 | A1 | 11/2015 |
| WO | 2015187366 | A1 | 12/2015 |
| WO | 2015187793 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2016181384 | A2 | 11/2016 |
| WO | 2017004278 | A1 | 1/2017 |
| WO | 2017089289 | A1 | 6/2017 |
| WO | 2017091624 | A1 | 6/2017 |
| WO | 2017105600 | A1 | 6/2017 |

(56) References Cited

FOREIGN PATENT DOCUMENTS

| WO | 2017184988 A1 | 10/2017 |
| WO | 2017187177 A1 | 11/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019043702 A1 | 3/2019 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2020124058 A1 | 6/2020 |
| WO | 2021011738 A1 | 1/2021 |

OTHER PUBLICATIONS

Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The Nice-Sugar (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A "Microbial Contamination of Haemodialysis Catheter Connections" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS.247VPC).
International Search Report and Written Opinion in PCT/US2008/079641 (Optis.203VPC) dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et. al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor, Glucon; retrieved on Dec. 29, 2010 from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.

(56)        References Cited

OTHER PUBLICATIONS

International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.
E. Atlas et al., "MD-Logic Artificial Pancreas System: A pilot study in adults with type 1 diabetes", Diabetes Care, vol. 33, No. 5, Feb. 11, 2010, pp. 1071-1076.
International Search Report and Written Opinion for the International Patent Application No. PCT/US2021/047690, mailed Jan. 14, 2022, 13 pages.
International Search Report and Written Opinion for the International Patent Application No. PCT/US2022/055745, mailed Feb. 14, 2022, 13 pages.
International Search Report and Written Opinion for the International Patent Application No. PCT/US2021/053162, mailed Mar. 28, 2022, 18 pages.
International Search Report and Written Opinion for the International Patent Application No. PCT/US2021/064041, mailed Apr. 29, 2022, 11 pages.
International Search Report and Written Opinion for the International Patent Application No. PCT/US2022/015809, mailed Jun. 20, 2022, 15 pages.
International Search Report and Written Opinion for International Patent Application No. PCT/US2022/029012, mailed Aug. 19, 2022, 12 pages.
European Search Report for the European Patent Application No. EP03743667, dated Jul. 22, 2008.
International Search Report and Written Opinion mailed Sep. 9, 2016, issued in PCT Patent Application No. PCT/US2016/037189, 12 pages.
Preliminary Report on Patentability mailed Dec. 21, 2017, issued in PCT Patent Application No. PCT/US2016/037189.
U.K. Intellectual Property Office, GB Application No. GB 1401587.9, "Search Report under Section 17(5)" Aug. 11, 2015, 1 page.
International Search Report and Written Opinion for PCT Application No. PCT/GB2015/050247, May 8, 2015, 14 pages.
Extended Search Report mailed Nov. 24, 2017, issued in European Patent Application No. 15779465.2, 10 pages.
International Search Report and Written Opinion for PCT Application No. PCT/US15/26875, mailed Jan. 18, 2016, 10 pages.

U.K. Intellectual Property Office, GB Application No. GB 1401588.7, "Search Report under Section 17(5)" Aug. 17, 2015, 1 page.
U.K. Intellectual Property Office, GB Application No. GB 1401589.5, "Search Report under Section 17" Jul. 27, 2015, 1 page.
International Search Report and Written Opinion for PCT Application No. PCT/GB2015/050250, May 7, 2015, 9 pages.
3GPP TS 23.003 V10.0.0.0 Numbering, addressing and identification. Dec. 2010.
International Search Report and Written Opinion for PCT Application No. PCT/GB2015/050251, Jun. 12, 2015, 9 bages.
European Search Report for the European Patent Application No. EP19194241, dated Oct. 22, 2019, 6 pages.
International Preliminary Report on Patentability for PCT/US2017/061095, issued on May 14, 2019, 6 pages.
International Search Report and Written Opinion for PCT/US18/52468, mailed on Feb. 26, 2019, 16 pages.
International Search Report and Written Opinion for PCT/US2017/061095, mailed on Feb. 20, 2018, 8 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.

(56)        References Cited

OTHER PUBLICATIONS

International Search Report and Written Opinion for International Patent Application No. PCT/US2021/051027, mailed on Jan. 7, 2022, 16 pages.

International Search Report and Written Opinion for International Patent Application No. PCT/US2021/052372, mailed Jan. 26, 2022, 15 pages.

International Search Report and Written Opinion for the International Patent Application No. PCT/US2021/046607, mailed Jan. 31, 2022, 20 pages.

International Search Report and Written Opinion for the International Patent Application No. PCT/US2021/055745, mailed Feb. 14, 2022, 13 pages.

International Search Report and Written Opinion for the International Patent Application No. PCT/US21/060618, mailed Mar. 21, 2022, 15 pages.

Herrero Pau et al.: "Enhancing automatic closed-loop glucose control in type 1 diabetes with an adaptive meal polus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

International Search Report and Written Opinion for the International Patent Application No. PCT/US2021/052855, mailed Dec. 22, 2021, 11 pages.

International Search Report and Written Opinion for the International Patent Application No. PCT/US2021/047771, mailed Dec. 22, 2021, 11 pages.

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2023/019254, mailed Jul. 25, 2023, 14 pages.

International Search Report and Written Opinion for the International Patent Application No. PCT/US2023/019256, mailed Jul. 10, 2023, 12 pages.

Maahs David M. et al: "A Randomized Trial of a Home System to Reduce Nocturnal Hypoglycemia in Type 1 Diabetes", Diabetes Care, vol. 37, No. 7, Jun. 12, 2014 (Jun. 12, 2014), pp. 1885-1891, Retrieved from the Internet: URL:https://diabetesjournals.org/care/article-pdf/37/7/1885/486685/1885.pdf>.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

"Read NFC Tags with an iPHone App on iOS 11", GoToTags, Sep. 11, 2017, web <https://gototags.com/blog/read-nfc-tags-with-an-iphone-app-on-ios-11/> (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

International Search Report and Written Opinion for Application No. PCT/US2019/030562, Sep. 25, 2019, 19 pages.

Lee, Melissa H. et al: "The Clinical Case for the Integration of a Ketone Sensor as Part of a Closed Loop Insulin Pup System",

(56)          References Cited

OTHER PUBLICATIONS

Journal of Diabetes Science and Technology Diabetes Technology Society, vol. 13(5), Dec. 31, 2019 (Dec. 31, 2019), pp. 967-973.

Rometo, David et al: "Perioperative Glycemic Management of Patients Undergoing Bariatric Surgery", Current Diabetes Reports, Current Science, Philadelphia, VA, US, vol. 16, No. 4, Feb. 15, 2016 (Feb. 15, 2016), pp. 1-8.

Andrenko et al., "EM Analysis of PBG Substrate Microstrip Circuits for Integrated Transmitter Front End" MMET Proceedings, 295-297 (2000).

Bardi et al., "Plane Wave Scattering From Frequency-Selective Surfaces by the Finite-Element Method" IEEE Transactions on Magnetics 38(2):641-644 (2002).

Chappell et al., "Composite Metamaterial Systems for Two-Dimensional Periodic Structures" IEEE, 3840387 (2002).

Cheng et al., "Preparation and Characterization of (Ba, Sr) TiO3 thin films using interdigitial electrodes" Microelectronic Engineering, 66:872-879 (2003).

Clavijo et al., "Design Methodology for Sievenpiper High-Impedance Surfaces: An Artificial Magnetic Conductor for Positive Gain Electrically Small Antennas" IEEE Transactions on Antennas and Propagation, 51(10):2678-2690 (2003).

Diaz et al., "Magnetic Loading of Artificial Magnetic Conductors for Bandwidth Enhancement" IEEE, 431-434 (2003).

Hansen "Effect of a High-Impedance Screen on a Dipole Antenna" IEEE Antennas and Wireless Propagation Letter, 1:46-49 (2002).

Joshi et al., "Processing and Characterization of Pure and Doped Ba0.6Sr0.4TiO3 thin films for tunable microsave applications" Mat. Res. Soc. Symp. Proc., 656E:DD4.9.1-DD4.9.6 (2001).

Kern et al., "Active Negative Impedance Loaded EBG Structures for the Realization of Ultra-Wideband Artificial Magnetic Conductors" IEEE, 427-430 (2003).

Kern et al., "The Synthesis of Metamaterial Ferrities for RF Applications Using Electromagnetic Bandgap Structures" IEEE, 497-500 (2003).

Kern et al., "Ultra-thin Electromagnetic Bandgap Absorbers Synthesized via Genetic Algorithms" IEEE, 1119-1122 (2003).

Kuhn et al., "Characterization of novel mono- and bifacially active semi-transparent crystalline silicon solar cells" IEEE Transactions on Electron Devices, 46(10): 2013-2017 (1999).

Kretly et al., "The Influence of the Height Variation on the Frequency Bandgap in an AMC, Artificial magnetic Conductor for Wireless Applications: an EM Experimental Design Approach" Proceedings SBMO/IEEE MTT-S IMOC, 219-223 (2003).

Lee et al., "Investigation of Electromagnetic Bandgap (EBG) Structures for Antenna Pattern Control" IEEE, 1115-1118 (2003).

McKinzie III et al., "Mitigation of Multipath Through the Use of an Artificial Magnetic Conductor for Precision CPS Surveying Antennas" IEEE, 640-643; Date of Conference: Jun. 16-21, 2002.

Monorciho et al., "Synthesis of Artificial Magnetic Conductors by Using Multilatered Frequency Selective Surfaces" IEEE Antennas and Wireless Propagation Letters, 1:196-1999 (2002).

Mosallaei et al. "Periodic Bandgap and Effective Dielectric Materials in Electromagnetics: Characterization and Applications in Nanocavities and Waveguides" IEEE Transcations on Antennas and Propagation, 51(3):549-563 (2003).

Pontes et al., "Study of the dielectric and ferroelectric properties of chemically processed BaxSr1-xTiO3 thin films" Thin Solid Films, 386(2)91-98 (2001).

Rogers et al., "AMCs Comprised of Interdigital Capacitor FSS Layers Enable Lower Cost Applications" IEEE, 411-414 (2003).

Sievenpiper et al., "Two-Dimensional Beam Steering Using an Electrically Tunable Impedance Surface" IEEE Transactions on Antennas and Propagation, 51(10):2713-2722(2003).

Sun et al., "Efficiency of Various Photonic Bandgap (PBG) Structures" 3rd Int'l. Conf. on Microwave and Millimeter Wave Technology Proceedings, 1055-1058 (2002).

Tsunemine et al., "Pt/BaxSr(1-x)TiO3/Pt Capacitor Technology for 0.15 micron Embedded Dynamic Random Access Memory" Jap. J. Appl. Phys., 43(5A):2457-2461 (2004).

Vest "Metallo-organic decomposition (MOD) processing of ferroelectric and electro-optic films: A review" Ferroelectrics, 102(1):53-68 (1990).

Viviani et al., "Positive Temperature Coefficient of Electrical Resistivity below 150k of Barium Strontium Titanate" J. Amer. Ceram. Soc. 87(4): 756-758 (2004).

Weily et al., "Antennas Based on 2-D and 3-D Electromagnetic Bandgap Materials" IEEE, 847-850 (2003).

Yang et al., "Surface Waves of Printed Antennas on Planar Artificial Periodic Dielectric Structures" IEEE Transactions on Antennas and Propagation 49(3): 444-450 (2001).

Zhang et al., "Planar Artificial magnetic Conductors and Patch Antennas" IEEE Transactions on Antennas and Propagation, 51(10):2704-2712 (2003).

Ziroff et al., "A Novel Approach for LTCC Packaging Using a PBG Structure for Shielding and Package Mode Suppression" 33rd European Microwave Conference—Munich 419-422 (2003).

International Search Report and Written Opinion for Application No. PCT/US17/61336, mailed on Jan. 25, 2018, 9 pages.

"Graph Chart." iconfinder.com. Aug. 15, 2016. Accessed Apr. 21, 2020. Available online at URL: https://www.confinder.com/iconsets/graph-chart-2>.

"Circular Progress Indicator Component for React." reactscript.com. Dec. 2, 2016. Accessed Sep. 9, 2020. Available online at URL: <http://reactscripts.com/circular-progress-indicator-component-react/>.

Kruska, Michal. "Circle progress bar." dribbble.com. Oct. 18, 2012. Accessed Apr. 21, 2020. Available online at URL: <https://dribbble.com/shots/775718-Circle-progress-bar>.

"C# custom control <circle progress bar) Xamarian Forms." stackoverflow.com. May 22, 2016. Accessed Apr. 21, 2020. Available online at URL: <https://stackoverflow.com/questions/37379868/c-sharp-custom-control-circle-progress-bar-xamarin-forms>.

International Search Report and Written Opinion for Application No. PCT/US2021/047685 mailed on Dec. 6, 2021, 15 pages.

"Circular Loader." dribbble.com. Nov. 19, 2015. Accessed Jul. 24, 2019. Available online at URL: https://dribbble.com/ shots/2362441-Circular-Loader (Year: 2015).

"Creating NSSlider with 2 knobs (range slider)." stackoverflow.com. May 6, 2015. Accessed Oct. 25, 2018. Available online at URL: <https://stackoverflow.com/questions/30082809/creating-nsslider-with-2- -knobs-range-slider> (Year: 2015).

"How to do a Round Slider." freecodecamp.org. Comment from Aug. 2018. Accessed Jul. 24, 2019. Available online at URL: https://www.freecodecamp.org/forum/t/how-to-do-a-round-slider/220375 (Year: 2018).

"Tick and cross circle shape icon . . ." depositphotos.com. Aug. 27, 2016. Accessed Feb. 1, 2019. Available online at URL :<https://depositphotos.com/121291612/stock-illustration-tick-and-cross-circle-shape.html> (Year: 2016).

"Vector-Vector Illustration of Preloader / Buffer Shapes, or Dials with Knobs." 123rf.com. Date not available. Accessed Oct. 25, 2018. Available online at URL: <https://www.123rf.com/photo_37292689_stock-vector-vector-illustration- -of-preloader-buffer-shapes-or-dials-with-knobs.html> (Year: N/A).

Gad, Tess. "Framer Cheat Sheet: Slider & Range Sliders." blog.framer.com. Jun. 12, 2017. Accessed Oct. 25, 2018. Available online at URL: <https://blog.framer.com/framer-cheat-sheets-slider-range-sliders-3dd2e5a4621d> (Year: 2017).

Obaizamomwan, Osas. "How to use the new features in iOS 9 Notes App." iphonehacks.com. Sep. 12, 2015. Accessed Apr. 24, 2018. Available online at URL: https://www.iphonehacks.com/2015/09/how-to-use-the-new-features-in-ios-9-notes-app.html.

International Search Report and Written Opinion for the International Patent Application No. PCT/US21/064056, mailed Apr. 4, 2022, 12 pages.

International Search Report and Written Opinion for the International Patent Application No. PCT/US21/064170, mailed Apr. 20, 2022, 12 pages.

Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/

(56)             References Cited

OTHER PUBLICATIONS blob/199ef86a900adf4b3d9c32f605eb11047bd3d62f/docs/EN/Module/
module.rst [retrieved on Apr. 11, 2022] the whole document.

Team Section—Qonto, by Christophe Kerebel, dated Dec. 12, 2018,
dribbble.com [online]. Retrieved Jul. 1, 2022 from Internet <URL:
https://dribbble.com/shots/5676730-Team-Section-Qonto> (Year: 2018).

Lee, et al. "The Clinical Case for the Integration of a Ketone Sensor
as Part of a Closed Loop Insulin Pump System," Journal of Diabetes
Science and Technology 2019, vol. 13(5) 967-973 (Year: 2019).

Laffel, et al., "ISPAD Clinical Practice Consensus Guidelines 2018:
Sick day management in children and adolescents with diabetes,"
Received: Jul. 19, 2018 (Year: 2018).

Mencher, et al., "Sick Day Management," First Online: Feb. 13,
2021, pp. 125-133. (Year: 2021).

Fuchs, et al. "Benefits and Challenges of Current Closed-Loop
Technologies in Children and Young People With Type 1 Diabetes,"
Mini Review published: Apr. 30, 2021 (Year: 2021).

* cited by examiner

INSULIN ADAPTATION AND SAFETY MONITORING

RELATED APPLICATIONS

This application claims the benefit of U.S. Provisional Patent Application No. 63/333,149, filed Apr. 21, 2022, the entire contents of which are incorporated herein by reference in their entirety.

BACKGROUND

Assessment of the performance of a medication delivery algorithm, such as automated drug delivery (ADD) algorithm, are often executed in a stepwise process, where a significant amount of insulin delivery data and glucose measurement data is processed. Changes in the ADD algorithm that can result in improved glucose control outcomes are applied. However, the processing of significant amount of data may result in a significant delay in the time that it takes for each ADD algorithm to improve its behaviors.

Ketogenic diets are high in fat, moderate in protein and low in carbohydrate content. Type 1 diabetic users following ketogenic diets have shown improvement in hemoglobin A1c (HbA1c) levels and reduced glycemic variability and weight loss. As compared to the benefits, a ketogenic diet poses risks in diabetic ketoacidosis (DKA) as well as hypoglycemia. To successfully benefit from a ketogenic diet, the risks of DKA and hypoglycemia should be controlled.

With regard to another subject, sodium-glucose cotransporter-2 (SGLT2) inhibitors have been effective oral medications which can be added to treat users with Type 2 diabetes, which is a disease that is inadequately treated with insulin. SGLT2 inhibitors have beneficial renal and cardiovascular outcomes and are favored by physicians. Type 2 diabetics have benefitted from low carb diets with HbA1c drops up to 34%, lower triglyceride levels, increased HDL levels compared to high carb diets. SGLT2 inhibitors inhibit glucose reabsorption by proximal renal tubules and lead to a switch from glucose to lipid utilization, thereby increasing ketones and decreasing the insulin-glucagon ratio. As a result, when taking SGLT2 inhibitors, a user's insulin needs and glucose levels behave differently on sick days. Risks of hypoglycemia, hyperglycemia as well as DKA (Diabetic Ketoacidosis) and euglycemic DKA (euDKA) increase. SGLT2 inhibitors might also be taken off label by Type 1 diabetics and presents risks of euDKA.

It would be beneficial if there was a system or a process by which the behavior of an ADD algorithm could be modified to account for the above issues with DKA and euDKA as well as addressing the challenges raised by use of SGLT2 inhibitors and diet changes resulting from fasting and food composition intake, such as a ketogenic diet.

BRIEF SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed is an example of a drug delivery system that includes a processor, a user interface, a memory, and communication circuitry. The processor is operable to execute programming instructions. The user interface includes a touchscreen display and user input circuitry. The memory is operable to store the programming instructions; and the communication circuitry is coupled to the processor and is operable to receive and transmit communication signals. The processor is operable to receive an indication that a user is starting a ketogenic diet. The processor retrieves a baseline total daily insulin value. The processor calculates a keto total daily insulin value using the retrieved baseline total daily insulin value; and utilizing the keto total daily insulin value in the calculation of a keto basal dosage of insulin or a keto bolus dosage of insulin.

Disclosed is an example of another drug delivery system that includes a processor, a user interface, a memory, and communication circuitry. The processor is operable to execute programming instructions. The user interface may include a display and user input circuitry. The memory is operable to store the programming instructions. The communication circuitry is coupled to the processor and is operable to receive and transmit communication signals. The processor may be operable to receive ketone levels from a ketone sensor. The processor may generate a prompt on the user interface inquiring whether a user's diet for today or another time period is a keto diet or a non-keto diet. The processor may adjust parameter settings and insulin delivery based on input received from the user via the user interface. Further, the processor, based on the received ketone levels of the user, may generate an indication of whether the user is adhering to a keto diet.

Disclosed is an exemplary controller of a drug delivery system. The controller may include a processor, a memory, and a communication circuitry. The processor may be operable to execute programming instructions. The memory may be operable to store the programming instructions. The communication circuitry may be coupled to the processor and be operable to receive and transmit communication signals. The processor, when executing the programming instructions, is operable to obtain ketone levels of a user. The obtained ketone levels may be evaluated with reference to a plurality of ketone thresholds. Based on the result of the evaluation, the processor may select a further action to be performed. The selected further action is at least one of generating a notification to seek medical attention, generating a notification to ingest food or drink such as carbohydrates, generating a notification to increase insulin, or a combination thereof. The processor may further cause performance of the selected further action.

DETAILED DESCRIPTION

The following discussion provides a framework to assess the behavior of a medication delivery algorithm (MDA) system in real time based on near-term retrospective drug delivery history (such as insulin delivery history) and glucose control outcomes through advisory mode assessments and describes the incorporation of changes to the MDA algorithm that retrospectively shows improved performance in historical data, which also holds promise in improving future delivery precision and outcomes as well.

The MDA system may implement, as the MDA algorithm, an "artificial pancreas" algorithm-based system, or more generally, an artificial pancreas (AP) application. For ease of discussion, the computer programs and computer applications that implement the medication delivery algorithms or applications may be referred to, interchangeably, herein as an "AP application," an "ADD algorithm," an "MDA algorithm," an "MDA application," or an MDA/ADD/AP application." An AP application may be configured to provide automated delivery of a drug, such as insulin, based on an analyte sensor(s) input, such as signals received from an analyte sensor(s), such as a continuous glucose monitor, or the like. The signals from the analyte sensor(s) may contain data indicative of glucose measurement values, timestamps, or the like.

Additionally, or alternatively, while the disclosed examples may have been described with reference to a closed loop algorithmic implementation, variations of the disclosed examples may be implemented to enable open loop use. The open loop implementations allow for use of different modalities of delivery of a drug(s) such as a smart pen, a syringe, or the like. For example, the disclosed AP application and algorithms may be operable to perform various functions related to open loop operations, such as the generation of prompts requesting the input of information such as diabetes type, weight, and/or age. Similarly, a dosage amount of a drug may be received by the AP application or algorithm from a user via a user interface. Other open-loop actions may also be implemented by adjusting user settings or the like in an AP application or algorithm.

Systems, devices, computer readable media and methods in accordance with the present disclosure are now described more fully hereinafter with reference to the accompanying drawings, where one or more examples are shown. The systems, devices, and methods described herein may be embodied in many different forms and are not to be construed as being limited to the examples set forth herein. Instead, these examples are provided so the disclosure is thorough and complete, and may fully convey the scope of the techniques and devices to those skilled in the art. Each of the systems, devices, media, and methods disclosed herein provides one or more advantages over conventional systems, components, and methods.

Figure 1:
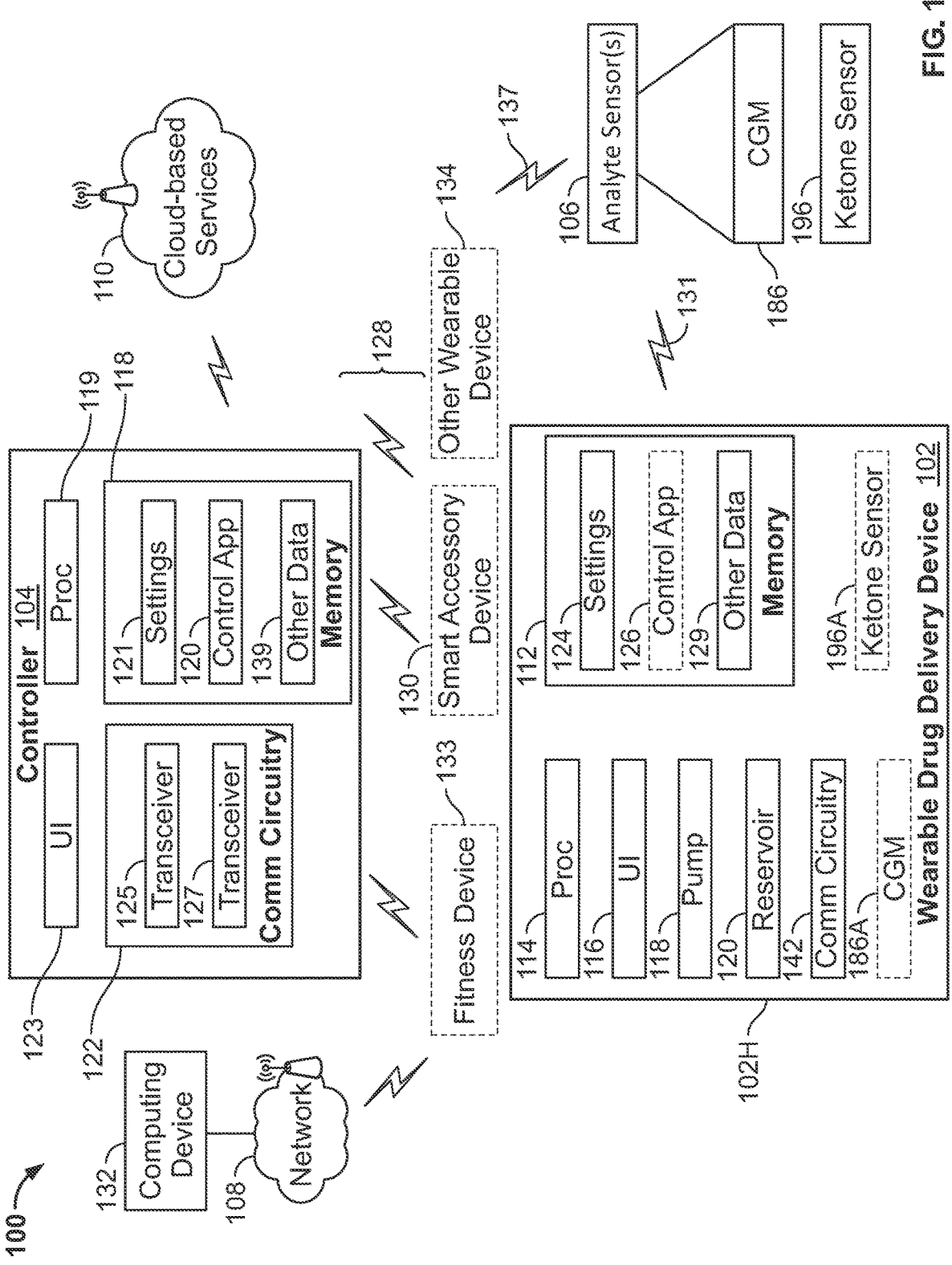
FIG. 1 illustrates an example of a system that is suitable to implement the subject matter described herein.

FIG. 1 illustrates a drug delivery system operable to implement the subject matter described herein. In some examples, the drug delivery system 100 is suitable for delivering insulin to a user in accordance with the disclosed embodiments utilizing the MDA/ADD/AP application as discussed above. The drug delivery system 100 may include a wearable drug delivery device 102, a controller 104 and an analyte sensor(s) 106, and other exemplary devices reflected in FIG. 1.

The wearable drug delivery device 102 may be a wearable device that is worn on the body of the user. The wearable drug delivery device 102 may be directly coupled to a user (e.g., directly attached to a body part and/or skin of the user via an adhesive, or the like). In an example, a surface of the wearable drug delivery device 102 may include an adhesive to facilitate attachment to the skin of a user.

The wearable drug delivery device 102 may include a processor 114. The processor 114 may be implemented in hardware, software, or any combination thereof. The processor 114 may, for example, be a microprocessor, a logic circuit, a field programmable gate array (FPGA), an application specific integrated circuit (ASIC) or a microprocessor coupled to a memory. The processor 114 may maintain a date and time as well as be operable to perform other functions (e.g., calculations or the like). The processor 114 may be operable to execute a control application 126 stored in the memory 112 that enables the processor 114 to direct operation of the wearable drug delivery device 102. The control application 126 may control drug delivery to the user per an ADD control approach as describe herein. For example, the control application 126 may be an ADD algorithm. The memory 112 may hold settings 124 for a user, such as specific factor settings, subjective insulin need parameter settings, ADD algorithm settings, such as maximum insulin delivery, insulin sensitivity settings, total daily insulin (TDI) settings and the like. The memory may also store other data 129, such as total daily insulin values, glucose measurement values from analyte sensor(s) 106 or controller 104, insulin dosage amounts (both basal and bolus) and the like from previous minutes, hours, days, weeks, or months. In an additional example, the analyte sensor(s) 106 may include multiple sensors, such as a continuous glucose monitor 186 and a ketone sensor 196. In an example of the multiple sensor arrangement, the analyte sensor(s) 106 may be operable to collect physiological condition data, such as ketone values (also referred to as "ketone level(s)"), ketone values with a time stamp, glucose measurement values (also referred to herein as "glucose values," or "glucose level(s)"), glucose measurement values and a timestamp, both ketone values and glucose values that may be shared with the wearable drug delivery device 102, the controller 104 or both. Alternatively, the ketone sensor 196 or CGM 186 may be separate sensors (and may be located separately on the user's body) and be configured to individually output measurement information (e.g., the above referenced ketone values, glucose measurement values and timestamp values or other data) to the controller 104 or wearable drug delivery device 102. The ketone sensor 196 may be configured to include hydrogel membranes that are used to improve ketone concentration and reduce electrode fouling. In a further example, the wearable drug delivery device 102 may optionally include a continuous glucose monitor 186A and/or a ketone sensor 196A, which may be removably incorporated in, on, or adjacent to, or fully integrated within the wearable drug delivery device 102. For example, the continuous glucose monitor 186A and/or the ketone sensor 196A may be incorporated in a housing 102H of the wearable drug delivery device 102. Note that ketones may also be detected using a breath sensor (which is not shown but may be incorporated in the controller 104) or urine content sensor (not shown); however, a subcutaneous ketone sensor as envisioned for ketone sensors 196 and 196A gives more accurate information and is usually near continuous. As described herein, the MDA algorithm of the control application 120 or 126 and drug delivery system 100 is described with the understanding that the ketone values are based on measurements made subcutaneously. Use of a ketone breath sensor or a urine sensor as part of or in addition to the analyte sensor(s) 106 may delay receipt of the ketone values and modifications to account for the delay may be incorporated into control application 120 and 126 of the drug delivery system 100.

For example, the communication circuitry 142 of the wearable drug delivery device 102 may be operable to communicate with the analyte sensor(s) 106 and the controller 104 as well as devices 130, 133 and 134. The communication circuitry 142 may be operable to communicate via Bluetooth, cellular communication, and/or other wireless protocols. While not shown, the memory 112 may include both primary memory and secondary memory. The memory 112 may include random access memory (RAM), read only memory (ROM), optical storage, magnetic storage, removable storage media, solid state storage or the like.

The wearable drug delivery device 102 may include a reservoir 120. The reservoir 120 may be operable to store drugs, medications, or therapeutic agents suitable for automated delivery, such as insulin, morphine, methadone, hormones, glucagon, glucagon-like peptide, blood pressure medicines, chemotherapy drugs, fertility drugs, arthritis drugs, combinations of drugs, such as insulin and glucagon-like peptide, or the like. A fluid path to the user may be provided via tubing and a needle/cannula (not shown). The fluid path may, for example, include tubing coupling the wearable drug delivery device 102 to the user (e.g., via tubing coupling a needle or cannula to the reservoir 120). The wearable drug delivery device 102 may be operable based on control signals from the processor 114 to expel the drugs, medications, or therapeutic agents, such as insulin, from the reservoir 120 to deliver doses of the drugs, medications, or therapeutic agents, such as the insulin, to the user via the fluid path. The processor 114 may be operable to cause insulin to be expelled from the reservoir 120.

There may be one or more communications links 128 with one or more devices physically separated from the wearable drug delivery device 102 including, for example, a controller 104 of the user/caregiver and/or a sensor 106. The communication links 128 may include any wired or wireless communication link operating according to any known communications protocol or standard, such as Bluetooth®, Wi-Fi, a near-field communication standard, a cellular standard, or any other wireless protocol. The analyte sensor(s) 106 may communicate with the wearable drug delivery device 102 via a wireless communication link 131 and/or may communicate with the controller 104 via a wireless communication link 137.

The wearable drug delivery device 102 may also include a user interface 116, such as an integrated display device for displaying information to the user, and in some embodiments, receiving information from the user. For example, the user interface 116 may include a touchscreen and/or one or more input devices, such as buttons, knob or a keyboard that enable a user to provide an input.

In addition, the processor 114 may be operable to receive data or information from the analyte sensor(s) 106 as well as other devices that may be operable to communicate with the wearable drug delivery device 102.

The wearable drug delivery device 102 may interface with a network 108. The network 108 may include a local area network (LAN), a wide area network (WAN) or a combination therein. A computing device 132 may be interfaced with the network, and the computing device may communicate with the insulin delivery device 102. The computing device 132 may be a healthcare provider device through which a user's controller 104 may interact to obtain information, store settings and the like. The ADD algorithm operating, as or in cooperation with, the control application 120 may present a graphical user interface on the computing device 132 enabling the input and presentation of information related to the ADD algorithm and the example techniques and processes described herein.

The drug delivery system 100 may include an analyte sensor(s) 106 for sensing the levels of one or more analytes of a user. The analyte levels may be used as physiological condition data and be sent to the controller 104 and/or the wearable drug delivery device 102. The sensor 106 may be coupled to the user by, for example, adhesive or the like and may provide information or data on one or more medical conditions and/or physical attributes of the user. The sensor 106 may be a continuous glucose monitor (CGM), such as 186, ketone sensor, such as 196, or another type of device or sensor that provides glucose measurements that is operable to provide glucose concentration measurements. The sensor 106 may be physically separate from the wearable drug delivery device 102 or may be an integrated component thereof. The sensor 106 may provide the processor 114 and/or processor 119 with physiological condition data indicative of measured or detected glucose levels of the user. The information or data provided by the sensor 106 may be used to modify an insulin delivery schedule and thereby cause the adjustment of drug delivery operations of the wearable drug delivery device 102.

The drug delivery system 100 may also include the controller 104. In the depicted example, the controller 104 may include a processor 119 and a memory 118. The controller 104 may be a special purpose device, such as a dedicated personal diabetes manager (PDM) device. The controller 104 may be a programmed general-purpose device that is a portable electronic device, such as any portable electronic device, smartphone, smartwatch, fitness device, tablet or the like including, for example, a dedicated processor, such as processor, a micro-processor or the like. The controller 104 may be used to program or adjust operation of the wearable drug delivery device 102 and/or the sensor 106. The processor 119 may execute processes to manage a user's glucose levels and for control the delivery of the drug or therapeutic agent to the user. The processor 119 may also be operable to execute programming code stored in the memory 118. For example, the memory 118 may be operable to store a control application 120, such as an ADD algorithm for execution by the processor 119. The control application 120 may be responsible for controlling the wearable drug delivery device 102, including the automated delivery of medicament, such as insulin, based on recommendations and instructions from the ADD algorithm, such as those recommendations and instructions described herein.

The memory 118 may store one or more applications, such as control application 120, and settings 121 for the insulin delivery device 102 like those described above. In addition, the memory 118 may be operable to store other data and/or computer programs 139, such as drug delivery history, glucose measurement values over a period of time, total daily insulin values, and the like. For example, the memory 118 is coupled to the processor 119 and operable to store programming instructions, such as the control application 120 and settings 121, and data, such as other data 139, related to a blood glucose of a user and/or data related to an amount of insulin expelled by the wearable drug delivery device 102.

The controller 104 may include a user interface (UI) 123 for communicating with the user. The user interface 123 may include a display, such as a touchscreen, for displaying information. The touchscreen may also be used to receive input when it is a touch screen. The user interface 123 may also include input elements, such as a keyboard, button, knob or the like. In an operational example, the user interface 123 may include a touchscreen display (including a display and user input circuitry, such as touch sensitive circuits and the like) controllable by the processor 119 and be operable to present a graphical user interface and receive inputs via the user input circuitry, the touchscreen display is operable to generate a signal indicative of the respective diet types, number of days, diet cycles, keto days, sick day mode, sickness symptoms, religious fasting mode, location information, calendar information, or the like. The touchscreen display, under control of the processor 119, may be operable to, in response to the received input, generate a response to a user's drug treatment regimen as well as cause the presentation of prompts on a graphical user interface as described with reference to the later examples described with reference to FIGS. 1-10. The graphical user interfaces discussed herein with respect to the later examples may be generated by the processor 119 of the controller 104 and be presented on the UI 123.

The controller 104 may interface via a wireless communication link of the wireless communication links 128 with a network, such as a LAN or WAN or combination of such networks that provides one or more servers or cloud-based services 110 via communication circuitry 122. The communication circuitry 122, which may include transceivers 127 and 125, may be coupled to the processor 119. The communication circuitry 122 may be operable to transmit communication signals (e.g., command and control signals) to and receive communication signals (e.g., via transceivers 127 or 125) from the wearable drug delivery device 102 and the analyte sensor(s) 106. In an example, the communication circuitry 122 may include a first transceiver, such as 125, that may be a Bluetooth transceiver, which is operable to communicate with the communication circuitry 122 of the wearable drug delivery device 102, and a second transceiver, such as 127, that may be a cellular or Wi-Fi transceiver operable to communicate via the network 108 with computing device 132 or with cloud-based services 110.

The cloud-based services 110 may be operable to store user history information, such as glucose measurement values over a set period of time (e.g., days, months, years), ketone levels over a set period of time (e.g., days, months, years), a drug delivery history that includes insulin delivery amounts (both basal and bolus dosages) and insulin delivery times, types of insulin delivered, indicated meal times, glucose measurement value trends or excursions or other user-related diabetes treatment information, specific factor settings including default settings, present settings and past settings, or the like.

Other devices, like smart accessory device 130 (e.g., a smartwatch or the like), fitness device 133 and other wearable device 134 may be part of the drug delivery system 100. These devices may communicate with the wearable drug delivery device 102 to receive information and/or issue commands to the wearable drug delivery device 102. These devices 130, 133 and 134 may execute computer programming instructions to perform some of the control functions otherwise performed by processor 114 or processor 119. These devices 130, 133 and 134 may include user interfaces, such as touchscreen displays for displaying information such as current glucose level, insulin on board, insulin deliver history, or other parameters or treatment-related information and/or receiving inputs, such as those described with reference to the examples of FIGS. 1-3. The display may, for example, be operable to present a graphical user interface for providing input, such as request a change in basal insulin dosage or delivery of a bolus of insulin. These devices 130, 133 and 134 may also have wireless communication connections with the sensor 106 to directly receive glucose level data or receive in parallel a presentation of the graphical user interface as shown in FIG. 1.

In another operational example, the controller 104 may be operable to execute programming code that causes the processor 119 of the controller 104 to perform the following functions. The processor 119 of the controller 104 may execute an ADD algorithm that is one of the control applications 120 stored in the memory or memory 118. The processor may be operable to present, on a user interface that is at least one component of the user interface 123. The user interface 123 may be a touchscreen display controlled by the processor 119, and the user interface 123 is operable to present a graphical user interface that offers an input of a subjective insulin need parameter usable by the ADD algorithm. The processor 119 may cause presentation on a user interface of a user device, a graphical user interface offering an input device that enables input of a subjective insulin need parameter. The ADD algorithm may generate instructions for the pump 118 to deliver basal insulin to the user or the like.

The processor 119 is also operable to collect physiological condition data related to the user from sensors, such as the analyte sensor(s) 106 or heart rate data, for example, from the fitness device 133 or the smart accessory device 130. In an example, the processor 119 executing the ADD algorithm may determine a dosage of insulin to be delivered based on the collected physiological condition of the user and a specific factor determined based on the subjective insulin need parameter. The processor 119 may output a control signal via one of the transceivers 125 or 127 to the wearable drug delivery device 102. The outputted signal may cause the processor 114 to deliver command signals to the pump 118 to deliver an amount of related to the determined dosage of insulin in the reservoir 120 to the user based on an output of the ADD algorithm. The processor 119 may also be operable to perform calculations regarding settings of the ADD algorithm as discussed as herein. Modifications to the ADD algorithm settings may be stored in the memory 118, for example, as settings 121.

A wearable drug delivery device 102, typically, has a lifecycle that is based on the amount of liquid drug that is stored in a reservoir 120 of the wearable drug delivery device 102 and/or the amount of the liquid drug delivered to the user. An ADD application or algorithm may use a number of parameters, such as glucose measurement values, total daily insulin, insulin onboard, and the like, when making the determination of an amount of the liquid drug to have delivered. In an operational example, the processor 119 of the controller 104 may be operable to receive evaluate the effectiveness of the ADD algorithm's control of the drug delivery device 102. For example, the processor 119 may be operable to utilize historical data accessible by the processor in an evaluation of past performance of the ADD algorithm and generate recommendations for adjusting settings of the ADD algorithm accordingly as described in more detail with reference to the examples of FIGS. 2 and 3).

While the system 100 is described with reference to delivery of insulin and the use of an ADD algorithm, the system 100 may be operable to implement a drug delivery regimen via a medication delivery algorithm using a number of different liquid or therapeutic drugs or medicaments. A liquid medicament or drug may be or include any medicament or drug in liquid form capable of being administered by a drug delivery device via a subcutaneous cannula, including, for example, insulin, glucagon-like peptide-1 (GLP-1) receptor agonist, pramlintide, glucose-dependent insulinotropic polypeptide (GIP), glucagon, co-formulations of two or more of glucagon, GLP-1, pramlintide, and insulin; as well as pain relief drugs, such as opioids or narcotics (e.g., morphine, or the like), methadone, blood pressure medicines, chemotherapy drugs, fertility drugs, or the like.

Insulin Adaptation and Safety Monitoring for Ketogenic Diets for Drug Delivery Systems In a common diet, a person intakes a moderate amount of carbohydrates, a moderate number of proteins, a moderate amount of fats, and a moderate amounts of other nutrients. In a person with diabetes, who is a user of a wearable drug delivery device, an ADD application monitors the user's glucose level and delivers medication that maintains the user's glucose level within a range of a glucose target set point.

When a user partakes in a ketogenic diet, the user intakes a higher amount of fat, a moderate amount of protein, and a low amount of carbohydrates. There are a number of benefits of a ketogenic diet, such as limited glucose spikes, weight loss, reduced need for medicament insulin, and others. Anecdotally, a ketogenic diet has been shown to reduce the need for medication, such as, insulin, by up to 40%.

Figure 2:
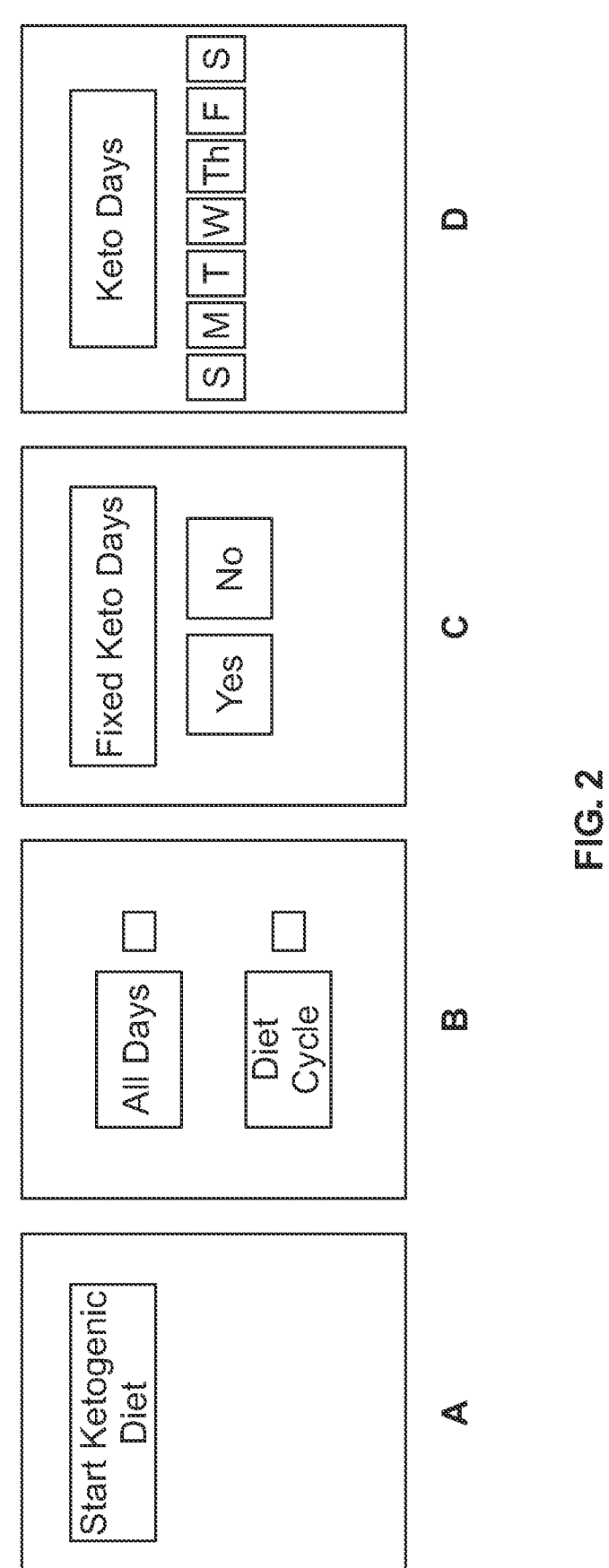
FIG. 2 illustrates exemplary graphical user interface windows and a process for setting up a schedule for indicating to a medication delivery system a user transition to a ketogenic diet.

The discussion of FIG. 2 illustrates examples of graphical user interfaces that enable a process for indicating to the control application of the medication delivery system in which the user is transitioning to a ketogenic diet. The safe medicament delivery is framed in the context of a drug delivery system, such as the example of FIG. 1.

The controller 104 of FIG. 1 may be operable to present a graphical user interface on the user interface 123. FIG. 2 illustrates an example of windows of a graphical user interface 200 that may be configured to enable a user to enter a "Keto mode" setup. In an example, a ketone diet may be considered to be less than 30 g of carbohydrates, with higher portions of fat and protein to make up enough for caloric needs. When the ketone diet is followed, the user's metabolism makes greater use of glycogen stores initially, after which stored fats are broken down by the liver into ketones that are used as an alternate energy source by the body. Even a low carbohydrate diet does not lead to the production of ketones. When setting up the exemplary Keto mode of the drug delivery system implemented via the control application 120, the user may set up Keto mode to indicate switching to a ketogenic diet. Referring to FIG. 2, in window A, the user may indicate to the system that the user intends to begin starting the ketogenic diet. In window B of the user interface 200, the user may either select an option to enter timing for a ketogenic diet for the whole week (e.g., "All days") or indicate a diet cycle. A commonly favored diet cycle is the 5:2 cycle. In this option, the person follows the Ketogenic diet for 5 days and switches to a higher carbohydrate diet on the other 2 days. Whatever the diet cycle selected by the user, it may have a constant pattern week to week or may change. An example of a change may be a user may select a 5:2 cycle for part of a month and switch to a different diet cycle for another part.

At window C of the user interface 200, the user may indicate to the control application 120, that the user intends to have fixed keto days by selection of the "Yes" or "No" buttons. The user interface (UI) 200 may transition from window C to window D, where the user is presented a graphical user interface that enables the user to input keto days that are days (represented by the first letter of the day starting at the left with S for "Sunday" and ending with at the right with S for "Saturday") the user intends to adhere to a keto diet. This enables the user to indicate to the control application the day the user intends to follow a variable diet cycle by selecting specific days as keto days. In a further example (not shown), a calendar may be presented the enables the user to indicate their diet cycle. Alternatively, the user may explicitly set the day as a specific keto day, for example at the beginning of the day (e.g., before breakfast) the user may indicate the day is a keto day. The control application may be operable to, according to a default or a user set notification schedule, present a graphical user interface so the control application can confirm with the user whether today is a Keto-Day first thing in the morning. Of course, the user has an option through the graphical user interface to end the ketogenic diet and return to a regular diet if desired at any time. With the keto day's indicated, the controller is operable to, based on the indication of the keto diet, the MDA algorithm may be operable to reduce the delivery of insulin to the user. This reduction in insulin delivery may be regardless of whether the user is a person with either type 1 diabetes or type 2 diabetes. The reduction in insulin delivery may be via a reduction in basal delivery, bolus dosages, or a combination of both as described below.

In an operational example, with reference to window A of FIG. 2, the processor may be operable to determine, based on an input received from a graphical user interface presenting on a touchscreen display, whether the user is starting a ketogenic diet. In response to the determination that the user is starting the ketogenic diet, the processor may present in window B of FIG. 2 a prompt to determine whether every day of the week is a ketogenic diet day or if the user is participating in a diet cycle (such as the 5 day: 2 day keto or the like). The processor, in response to the determination that the user is participating in the diet cycle, may be operable to generate, as shown in window C of FIG. 2, a prompt for an indication of whether the ketogenic diet is on fixed days of the week. In response to an indication that the ketogenic diet is on fixed days of the week, the processor as shown in window D of FIG. 2, may be operable to present an interactive calendar with days of the week for selection by a user.

Additionally, or alternatively, the control application may be configured to respond to frequent changes between keto and non-keto diet on a meal-to-meal basis. For example, a user may turn off keto mode multiple times throughout the day but may, for example, be prompted to adjust the bolus number (e.g., a dosage and frequency of the bolus). If the user is switching their diet cycle mode on a meal-to-meal (i.e., keto to non-keto) basis, the algorithm may be operable to focus on adapting the bolus number (e.g., the number of boluses and/or the dosage amount per bolus). The GUI may include an indication of the meal mode, such as a Keto Diet banner on a main screen of the GUI when in either the Keto meal mode or a Non-Keto (or Regular) meal mode.

For example, when a user is cycling between a keto and non-keto diet either every day or several times a week or the like, the Drug delivery system may cause the presentation of the graphical user interface (GUI) on a controller. The user may select the diet cycle via an input to the UI 200, such as a ketogenic diet cycle. Other types of diets may also be presented, such as Paleo diet, vegan diet, or the like, and these may be referred to as a "diet mode" selectable by a user. The particular days or times or meals for which the user is following the particular diet may be referred to as a diet cycle. In a specific example, when the Ketogenic diet is selected as a diet mode in a diet cycle, the days which are non-keto days may utilize the baseline TDI values with the basal again calculated as 0.5*TDI/24 units/hour and the bolus amounts being x % of TDI with x varying from 3% to 10% with larger ranges possible based on personalization. Of course, the value 0.5 may be modified based on the user's time in range (e.g., 110-150 mg/dL of glucose).

The described drug delivery system may be operable to provide ketone monitoring via, for example, by the ketone sensor 196 of FIG. 1. For example, under regular carbohydrate ingestion, glucose is the main substrate for glycolysis, which results in the production of adenosine triphosphate (ATP), the body's main energy source. However, under conditions of carbohydrate restriction (>48-72 hours or the like) liver glycogen stores get depleted. Without glucose as a substrate for ATP production, the liver breaks down triglycerides to make ketone bodies to travel to target tissues (e.g., brain, muscles) and generate ATP. This process of ketogenesis may be regulated by insulin; the low carbohydrate levels leading to low insulin levels, which in turn promotes ketosis.

In some examples, a drug delivery system may be equipped with a continuous ketone sensor. For example, the continuous ketone sensor and the continuous glucose monitor (CGM) may be integrated within the insulin delivery system as one physical unit. The continuous ketone sensor may determine a concentration of the enzyme 3-hydroxybutyrate by detecting and measuring the 3-hydroxybutyrate dehydrogenase (3HBDH). Examples of ketone levels and their corresponding physiological status for nutritional ketosis are summarized in Table 1 below:

| Physiological Status | Ketone Level |
|---|---|
| Nutritional Ketosis | 0-1.4 mmol/L |
| Optimal Ketosis | 1.5-3.0 mmol/L |
| Diminishing Returns | 3 mmol/L |
| Danger | 10 mmol/L |

Where Ketosis=generation of ketones and nutritional ketosis is for users that on a keto diet, the body is changing and instead of using carbs, the liver is breaking down fat to produce energy, and as a result the user's ketone levels are low. Low ketone levels may be a new normal parameter for people who start a keto diet. If the person stays on the keto diet, it is presumed the user's ketone generation eventually elevates to "Optimal Ketosis" levels (1.5-3.0 mmol/L). When ketone levels rise over 3 mmol/L, the diet is providing diminished returns and the user may begin to experience progressive symptoms of nausea and diarrhea to vomiting and more extensive diarrhea as well as other physiological changes. As shown in the process examples herein, if a user's ketone levels go above 3 mmol/L, the control application may be configured to evaluate the amount of insulin delivered to the user (over a preset period of time) to determine whether additional insulin should be delivered, or provide a prompt via a graphical user interface on the user interface for the user to ingest additional carbohydrates. In one or more examples, the processor may be operable to detect automatically whether the user is adhering to a keto diet. In some examples, the processor by executing the algorithm may be able to use on the ketone sensor to determine the user's adherence to the keto diet. The algorithm may also be operable to determine adherence to the keto diet without a ketone sensor. For example, the algorithm may be operable to cause the processor to evaluate the BG pattern and total daily insulin (TDI) for a given period of time, such as 3 hour, 10 hours or the like. An alert may be generated to indicate that the user is not adhering to their keto diet, when the TDI increases upwards of approximately 67%.

The processor based on the disclosed algorithm, may be operable to adapt the basal and bolus insulin doses as the user transitions to a ketogenic diet by determining a reduction in TDI (e.g., approximately 60%). For example, TDI may initially be reduced by 40% on day 1 of the keto diet, then on day 2 and subsequent days of being on the keto diet, the basal and bolus insulin for the prior day is used to calculate TDI. The processor may be operable to predict basal and bolus insulin doses based on a different TDI input.

With regard to insulin adaptivity, as the user transitions from a regular diet to a ketogenic diet, both basal insulin and bolus insulin need to be reduced. Typical reductions in basal insulin on a ketogenic diet from baseline may be 10% to 20% or more. Total daily insulin (TDI) requirements have been observed to drop by as much as 44% compared to baseline when on a ketogenic diet. Accordingly, the ketogenic diet TDI setting may be reduced by approximately 44%. In some embodiments, the processor may reduce the TDI by a lesser amount, say 15% to 20% initially, and gradually reduce TDI further up to approximately 40%—approximately 44%, or the like, from baseline as the Keto diet pattern is stabilized. The control application may monitor the user's ketone levels and glucose levels to ensure the user is staying within the optimal ketone range (e.g., 1.5-3.0 mmol/L). Based on the results of the monitoring, the control application may determine whether insulin (either basal and/or bolus) needs to be increased or further reduced. For example, the 15%-20% reduction in TDI may be modified based on levels of ketones and the user's glucose levels detected by a ketone sensor and a CGM. Frameworks for insulin adaptivity are discussed below and shown in FIGS. 3-6.

Figure 3:
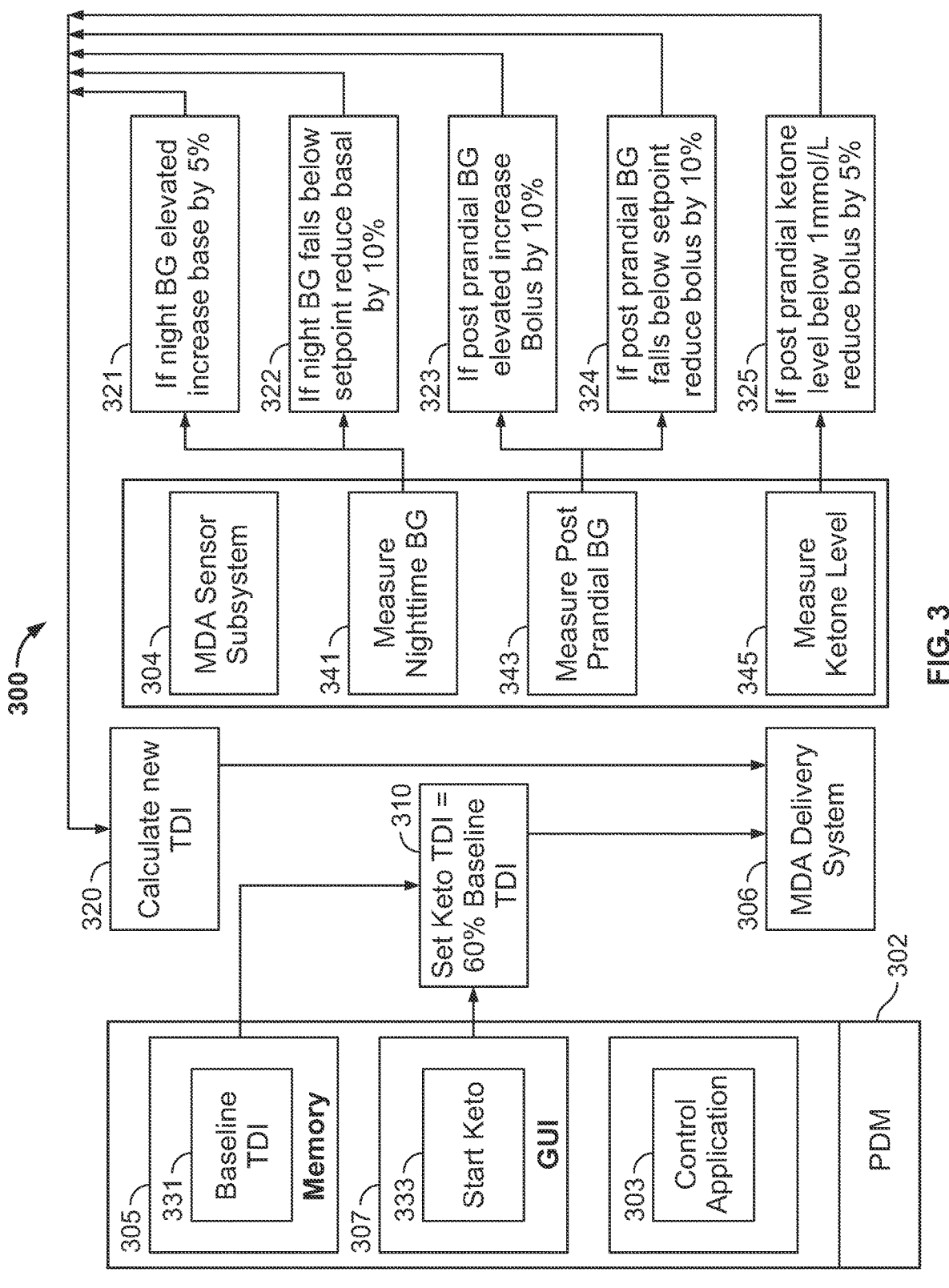
FIG. 3 illustrates an exemplary technique for modifying a drug delivery parameter of a drug delivery system when a user switches to a ketogenic diet.

FIG. 3 illustrates an example technique that may be implemented by a control application of a drug delivery system when a user switches from a regular or non-ketogenic diet to a ketogenic diet. For example, after the user selects to enter "keto mode," for example, and/or indicates the respective days of a keto diet, the controller may adjust parameters or settings (e.g., 121, 124 or both of FIG. 1) of the control application.

As shown in FIG. 3, a user may switch to a ketogenic diet and enter a "keto mode" or "ketogenic diet mode." The technique 300 may be implemented when a user makes the switch to a ketogenic diet. In response to the indication that the user is following a ketogenic diet, the control application adjusts settings to correspond with the user's expected, reduced insulin needs. As the user's carbohydrate intake is reduced, the insulin delivered by the drug delivery system may be reduced a corresponding amount, or alternatively may be reduced by a reduction factor, to avoid the risk of hypoglycemia. As hypoglycemia is a primary risk in the transition to a ketogenic diet, the example technique 300 as executed by a processor may enable safe insulin delivery while monitoring the user's glucose and ketone levels.

The example technique 300 may include the interaction between a smartphone or a personal diabetes management device (PDM) 302, the MDA sensor subassembly 304 and MDA delivery system 306. The PDM 302 may be the same as or at least similar to the controller 104 of FIG. 1. For example, the PDM 302 may include a control application 303, a memory 305 and graphical user interface 307. The MDA delivery system 306 may be a wearable drug delivery system, such as wearable drug delivery system 102 of FIG. 1, or the like.

The control application 303 in response to the "start keto" indication 333 or entering "keto mode" (as described with reference to FIG. 2) via the GUI 307 may obtain a baseline total daily insulin (TDI) 331 from memory 305. The baseline TDI may be, for example, be the most recent TDI setting for the user regardless of whether it is a TDI for a regular diet day or a Keto diet day. Baseline TDI may differ from one user to another user. Starting with the baseline TDI 331 and at the onset of a ketogenic day (e.g., Keto day), the Keto TDI may be set to approximately 60% of the baseline TDI. After 310, the Keto TDI may be provided to the MDA delivery system 306. The MDA delivery system 306 may be operable to use the Keto TDI to calculate basal and bolus dosages of insulin. For example, a keto-adjusted basal rate delivery may be set to 0.5*Keto TDI/24 units/hour. In the example, the MDA sensor subsystem 304 may include a processor that is operable to measure different physiological aspects of the user's blood. For example, the measurement of glucose following meals may be used to adjust bolus insulin delivery. A bolus dosage can be calculated as x % of TDI based on meal announcement. Typical values of x may range from 3% to 10% and may be personalized for larger ranges (e.g., 3%-15%). Closed loop drug delivery systems may continue to deliver insulin based on glucose trends and MDA algorithm constraints. But with the Keto TDI that is reduced from the baseline TDI, the risk of hypoglycemia is significantly reduced. In some examples, ketone levels as well as glucose levels may be monitored continuously by the MDA sensor subsystem 304. The MDA sensor subsystem 304 may include a ketone sensor and a glucose sensor (such as those described with reference to FIG. 1) as well as other sensors, such as a blood oxygen sensor, a heart rate sensor, and the like, the outputs of which are provided to the control application 303 of the PDM 302.

In an example, the MDA sensor subsystem 304 may be operable to make measurements of nighttime glucose (e.g., 2:00 am or the like), via the measured nighttime glucose process 341, that may be used to further alter the Keto-adjusted basal rate. In the example, at 321, the processor may be operable to increase the Keto-adjusted basal rate by 5% or the like, if the measured nighttime glucose is elevated (e.g., +10-20 mg/dL or greater) above the user's target set point (e.g., 110 mg/dL). This change at 321 indicates that basal insulin delivery was not sufficient.

Alternatively, at 322, if the measured nighttime glucose falls (e.g., −15-25 mg/dL or more) below the user's target set point (e.g., 110 mg/dL), the processor may reduce the keto-adjusted basal dosage by 10% or the like. This change at 322 indicates that basal insulin delivery was greater than needed for the user.

The MDA sensor subsystem 304 when performing the process 300 may also be operable to measure a user's post prandial glucose via a measured post prandial glucose process 343. The control application 303, in response to receiving the measured post prandial glucose, the control application 303 may, at 323, increase the bolus dosage by 10%, if the post prandial glucose is elevated a predetermined amount, such as by 10-20 mg/dL or greater. Alternatively, the control application 303, in response to receiving the measured post prandial glucose, the control application 303 may, at 324, reduce the bolus dosage by 10%, if the post prandial glucose falls a predetermined amount, such as by 10-20 mg/dL or more.

The MDA sensor subsystem 304 when performing the process 300 may also be operable to measure a user's post prandial ketone levels via a measure ketone level process 345. In response to the measured post prandial ketone levels, the control application 303 may be execute, at 325, a subprocess. In the subprocess at 325, if the post prandial ketone levels are low (e.g., 1 mmol/L), the control application 303 may reduce the bolus insulin to promote ketosis and safeguard against hypoglycemia. The output of whichever subprocess is executed at any of 321, 322, 323, 324 or 325 may be used by the control application 303 at 320 to calculate a new TDI. For example, the total insulin delivered via basal and bolus may be added to reestablish the new TDI. The new TDI may be used in calculations performed the next day. For example, the new TDI may be substituted for the baseline TDI 331 or may replace the baseline TDI 331 in the memory 305, where it would be used to set a Keto TDI in response to a start keto 333 indication.

Figure 4:
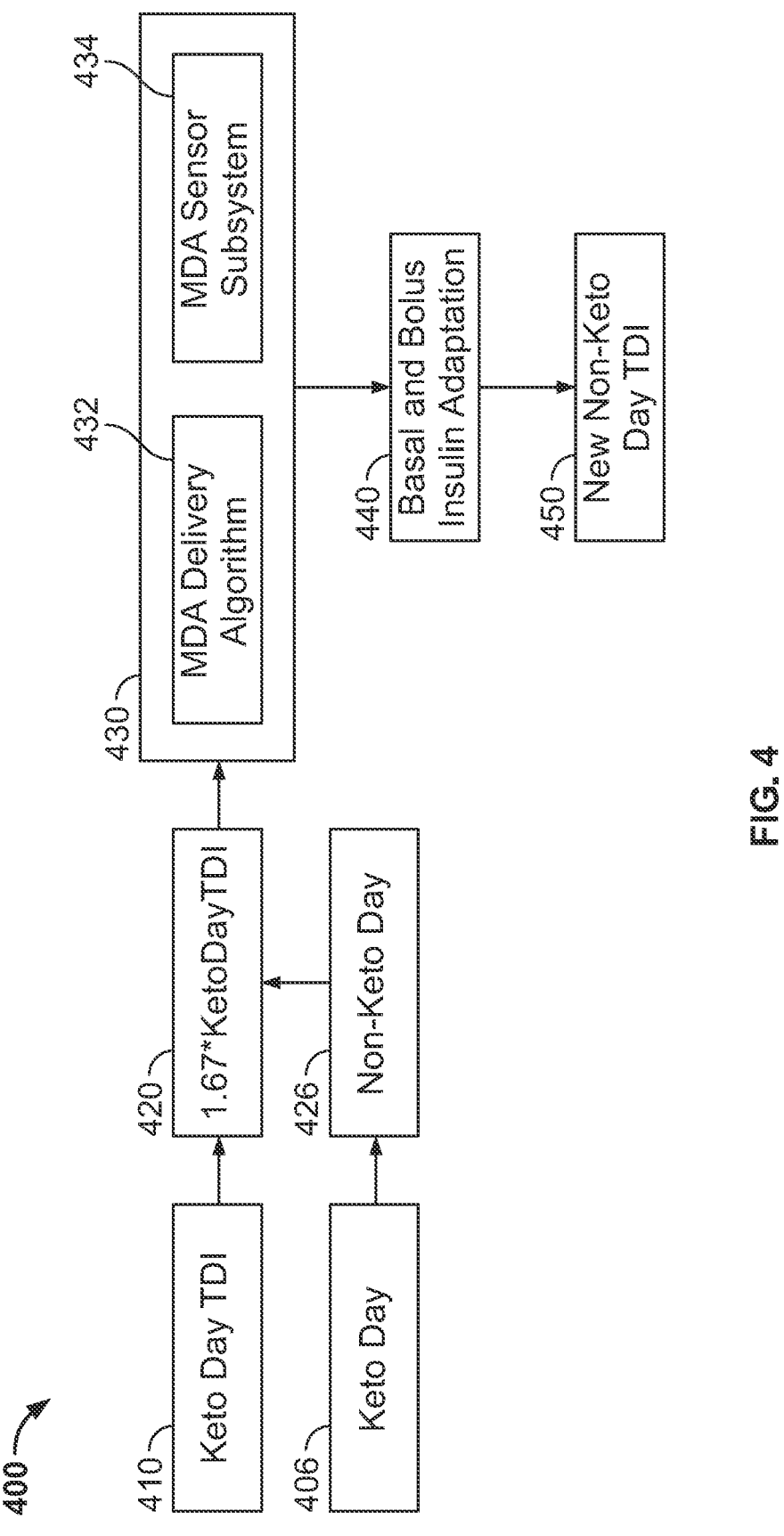
FIG. 4 illustrates an exemplary process flow diagram for a user's transition from a ketogenic diet day to a non-ketogenic diet day.

FIG. 4 depicts an example diet cycle transition process from a ketogenic day diet back into a non-keto day of a diet cycle.

It is anticipated that users may alternate between consuming a ketogenic diet on some days (e.g., "Keto day(s)") and partaking in a non-ketogenic diet on other days (e.g., "Non-Keto day(s)"). To enable the MDA delivery system to accommodate this change in diet, an example diet cycle transition process 400 that utilizes the user interface of a controller, such as 104 of FIG. 1, to receive an indication of the change from a Keto day to a Non-Keto day, and this diet cycle transition process may be executed by a processor. In FIG. 4, the user is currently adhering to a keto day diet, but will be transitioning to a non-keto day diet. When the user is adhering to the keto day diet, the diet setting for the MDA delivery algorithm is a keto day 406 and the corresponding TDI setting is the keto day TDI setting 410. For example, the keto day 406 setting may include a keto day TDI 410 value that is determined based on historical data related to the user's glucose levels, meal-related data, such as carbohydrates, protein, and fat content of meals and the like, as well as other data (e.g., exercise history, ketone levels and the like). Recall that when a user is adhering to their keto diet, the keto day TDI 410 value is less than a non-keto day TDI value. In response to the keto day 406 setting, a processor, such as 119 or 114 of FIG. 1, may be operable to determine a keto day TDI value based on historical data related to the user's glucose levels, meal-related data, such as carbohydrates, protein and fat content of meals and the like, as well as other data (e.g., exercise history, ketone levels and the like).

In the diet transition example, the system setting for the user's total daily insulin (TDI) may be the keto day TDI setting 410. A user may indicate to the MDA delivery system that the present day is a non-keto day via a non-keto day input 426 to the user interface (not shown in this example). In response, a processor executing the MDA delivery algorithm 432 may calculate a modified TDI as the non-keto day TDI using the keto day TDI. For example, the processor may calculate the non-keto day TDI as 1.67*Keto TDI as a modified TDI 420. The factor 1.67 may be tuned based on different user parameters and user adherence to the respective indicated diet day (i.e., keto day or non-keto day). Since the user was previously adhering to a keto diet in this example shown in FIG. 4, the baseline TDI is the determined Keto day TDI 410. At 430, the MDA algorithm 432 may utilize the modified TDI 420 and inputs from the MDA sensor subsystem 434 (e.g., ketone monitor, glucose monitor (including a CGM) and the like) to determine a modified treatment plan. For example, the MDA delivery algorithm 432, at 440, may determine adaptations to the user's non-keto day basal dosage and basal delivery rate as well as adaptations to the user's non-keto day bolus dosages, delivery rates and delivery schedules (i.e., basal and bolus insulin adaptation). At 450, the MDA delivery algorithm 432 executed by the processor may calculate a new non-keto day TDI based on the adaptations made to the non-keto day basal dosage and basal delivery rate and the user's keto day bolus dosages, delivery rates and delivery schedules at 440.

If a non-keto day continues the next day the new non-keto day TDI determined at 450 becomes (i.e., non-keto day TDI) will be the baseline TDI, such as 410, to be used for the next day as well, whether it is a repeat of the non-keto day or a start of a new keto day.

Figure 5:
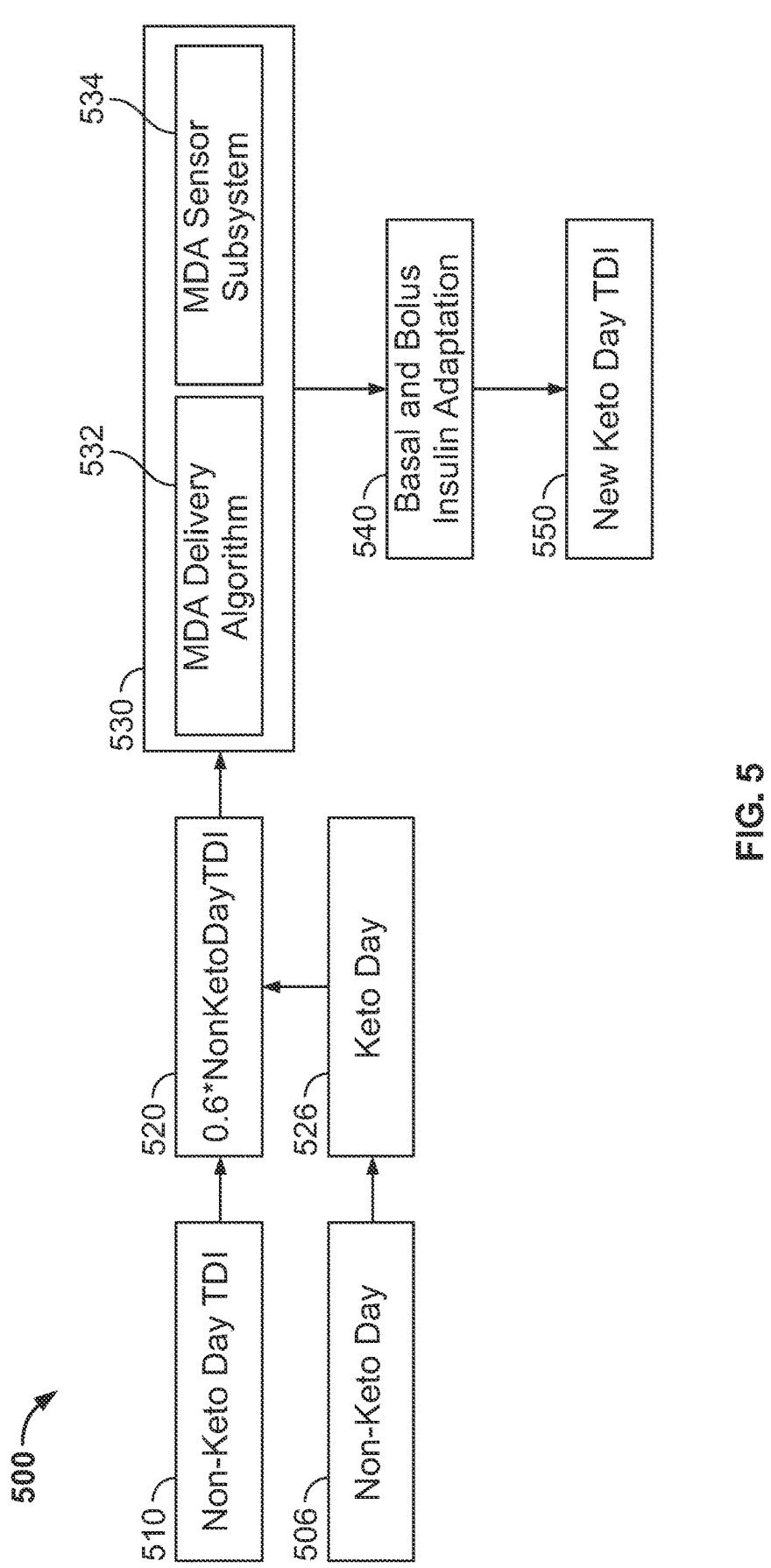
FIG. 5 depicts an exemplary process flow diagram for a user's transition from a non-ketogenic diet day to ketogenic diet day.

FIG. 5 depicts an example diet cycle transition from a non-ketogenic day diet back into a ketogenic day of the diet cycle. To enable the MDA delivery system to accommodate this change in diet, another example of a diet cycle transition process 500 that utilizes the user interface of a controller, such as 104 of FIG. 1, to receive an indication of a change in diet from a non-keto day to a Keto day may be executed by a processor. For example, when adhering to a non-keto day diet, the diet setting for the ADD delivery algorithm is a non-keto day 506 and the user's total daily insulin (TDI) may be the non-keto day TDI 510. Recall that when a user is adhering to their non-keto diet, the non-keto day TDI setting is typically greater than a keto day TDI setting. The non-keto day 506 setting may include the non-keto day TDI 510. A user may indicate via a keto day input 526 to the user interface (not shown in this example) to the MDA delivery system that today is "a non-keto day," which indicates the diet for the present day is a non-ketogenic diet. In response to the non-keto day 506 setting, a processor, such as 119 or 114 of FIG. 1, executing the MDA delivery algorithm 532 may calculate the modified TDI 520 based on historical data related to the user's glucose levels, meal-related data, such as carbohydrates, protein and fat content of meals and the like, as well as other data (e.g., exercise history, ketone levels, and the like). For example, the processor may calculate the modified TDI 520 as, for example, 0.6*Non Keto Day TDI. The factor 0.6 may be tuned based on different user parameters and user adherence to the respective indicated diet day (i.e., keto day or non-keto day).

Since the user was previously adhering to a keto diet in this example shown in FIG. 5, the baseline TDI is the determined non-Keto TDI 510. At 530, the MDA algorithm 532 may utilize the modified TDI 520 and inputs from the ADD sensor subsystem 534 (e.g., ketone monitor, glucose monitor (including a CGM) and the like) to determine a modified treatment plan. For example, the MDA delivery algorithm 532 may determine, at 540, adaptations to the user's non-keto day basal dosage and basal delivery rate as well as adaptations to the user's non-keto day bolus dosages, delivery rates and delivery schedules (i.e., basal and bolus insulin adaptation). At 550, the MDA delivery algorithm 532 executed by the processor may calculate a new keto day TDI based on the adaptations made to the keto day basal dosage and basal delivery rate and the user's non-keto day bolus dosages, delivery rates and delivery schedules at 540.

In the example, if a keto day continues the next day, the new keto day TDI from 550 will be the baseline TDI to be used by the MDA delivery algorithm 532 for the next day. And the keto TDI or baseline TDI may be adjusted as explained above to account for the keto day continuing to the next day.

When implementing ketone monitoring, ketone levels are typically approximately <0.5 mmol/L to approximately 1.0 mmol/L. Exercise may elevate ketone levels further by up to approximately 0.5 mmol/L for moderate exercise. Exercise may further elevate ketone levels with levels going up to approximately 3 mmol/L. Ketone levels are also increased under low carbohydrate diets. Under regular carbohydrate ingestion, glucose is the main substrate for glycolysis, resulting in the production of adenosine triphosphate (ATP), the body's main energy source. However, under conditions of carbohydrate restriction (>48-72 hours) liver glycogen stores get depleted. Without glucose as a substrate for ATP production, the liver breaks down triglycerides to make ketone bodies to travel to target tissues (e.g., brain, muscles) and generate ATP. This process of ketogenesis is regulated by insulin; the low carbohydrate levels leads to low insulin levels, which in turn promotes ketosis. Starvation ketosis may elevate ketone levels up to a concentration of 5 mmol/L.

In either transition illustrated in FIG. 4 or FIG. 5, the monitoring of the ketone levels as well as the TDI trends may be used to determine how well the user is maintaining their time within range of their target glucose setpoints or another metric. If the ketone levels are between, for example, approximately 1.5 mmol/L to approximately 3 mmol/L for post meal periods, the MDA system may determine that the ketosis is optimal. However, if the user's TDI falls over a period of time, the MDA system may determine that the insulin requirements are reducing (which may be because of reduction in insulin resistance as well as a user's weight loss).

Figure 6:
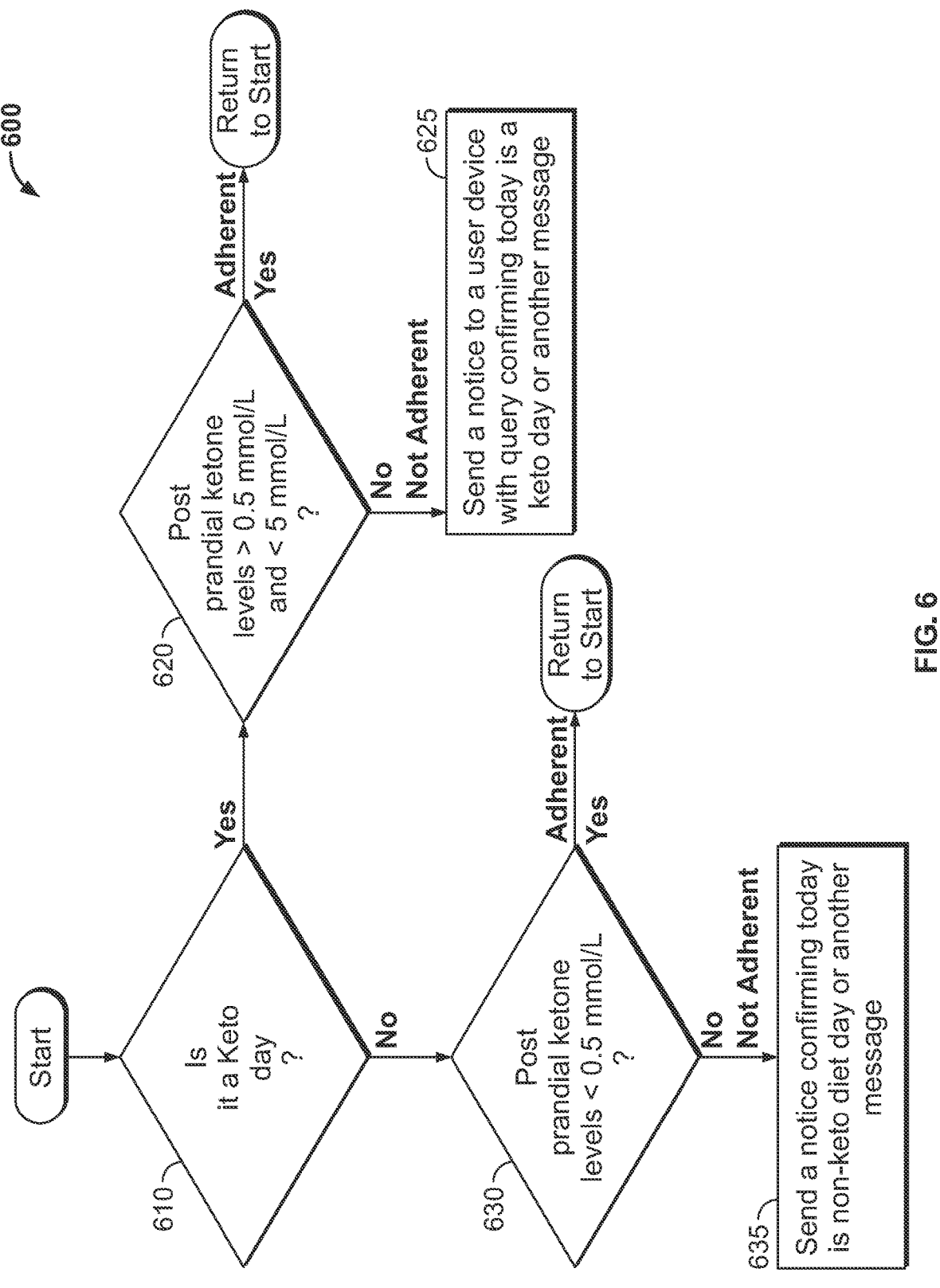
FIG. 6 illustrates a flowchart of an exemplary process for monitoring a user's adherence to their diet.

FIG. 6 illustrates a flowchart of an example process for monitoring a user's adherence to their ketogenic diet. A control application executed by a processor of MDA system, such as the processor 119 of the controller 104 of FIG. 1, may be operable to monitor adherence of the users to the designated ketogenic diet by measuring and evaluating the user's ketone level. For example, the processor may prompt the user to indicate, at 610, whether the day's (or another time period) diet is a keto diet day (i.e., keto day). If, in response to the prompt, the processor receives an affirmative response, the process 600 may proceed to decision 620. Instead of the control application prompting the user, the control application may retrieve information obtained via the GUI 200 to determine whether today is a keto diet day. At 620, the processor may determine if the post meal ketone levels are between a preset range, such as, for example, approximately 1.5 mmol/L to approximately 3 mmol/L (which indicates optimal ketosis) or approximately 0.5 mmol/L to approximately 5 mmol/L. In response to the post meal ketone levels being determined to be between the preset range, the processor may determine that there is good adherence to the diet and return to the beginning of the process 600. Alternatively, if the post prandial ketone levels are not within the preset range at 620, the processor may determine the user is not adhering to the ketogenic diet and, at 625, sends a query or the like to a user device confirming with the user that today is a keto day.

Returning to step 610, if the user indicates to the processor that today is not a keto diet day, the processor may proceed to step 630. At 630, the processor may determine whether the post meal ketone levels are below a minimum value or lower boundary of the preset range, such as, for example, 0.5 mmol/L or the like. In response to a determination that the post meal (i.e., post prandial) ketone levels are less than the minimum value or the lower boundary, it is likely that the user is adhering to a non-ketogenic diet (i.e., a "YES" at 630). In response to such a determination, at 635, the process 600 may restart. Alternatively, at 630, if the post meal (i.e., post prandial) ketone levels are determined to be greater than the minimum value or lower boundary and the determination indicates that "NO" the user is not adhering to a non-ketogenic diet, the processor may send a notice confirming today is a non-keto diet day. For example, the process 600 may cause the generation of a pop-up menu to confirm with the user whether they are adhering to the expected diet plan.

Diabetic Ketoacidosis (DKA) Monitoring: The ketone levels and glucose levels may be monitored to detect incipient DKA, and if incipient DKA is detected, a prompt response may be carried out by the MDA system, for example, by delivering an insulin bolus and/or increasing the user's basal rate temporarily. Diabetic ketoacidosis, also known as DKA, is a buildup of acids in your blood. It can happen when your blood sugar is too high for too long. DKA is a serious complication of diabetes and could be life-threatening.

Figure 7:
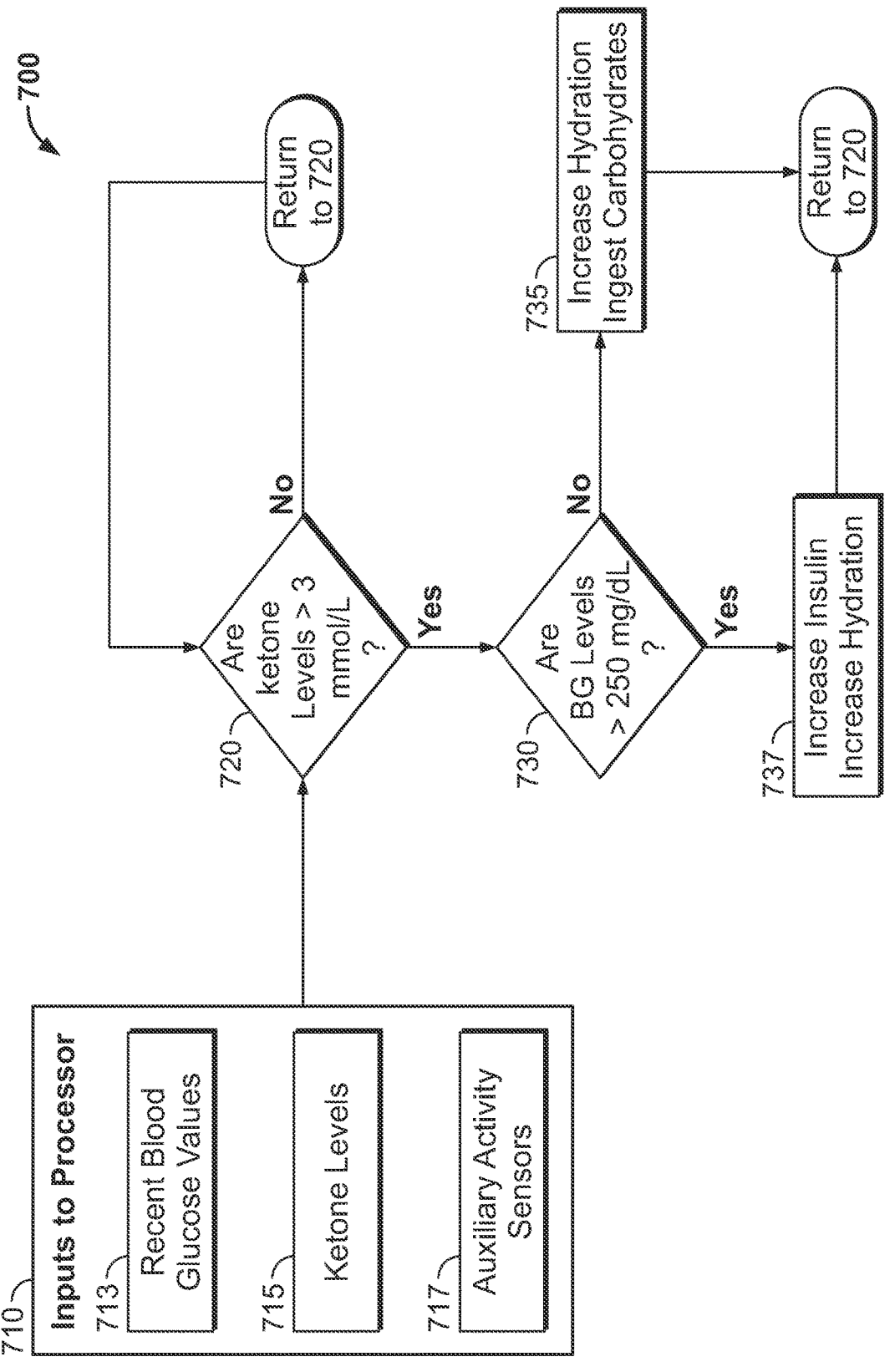
FIG. 7 illustrates a flowchart of an exemplary process for monitoring and intervening steps for avoiding diabetic ketoacidosis.

FIG. 7 illustrates a flowchart of a process for monitoring and intervening steps for avoiding diabetic ketoacidosis (DKA). The monitoring of DKA includes a processor, an algorithm (such as 700 represented by programming code and stored in memory (not shown in this example)), and at least one or more inputs to a processor 710, such as recent glucose values 713, ketone levels 715 and auxiliary activity sensors 717, such as a smart watch, a heart rate monitor, a fitness device (e.g., wearable on the wrist), a global positioning system device, and the like. In the process 700, the processor may obtain ketone levels 715 from a memory or from a ketone sensor. At decision block 720, if the ketone levels 715 are, for example, greater than (>) 3 mmol/L, the processor may interpret this result as a sign that the ketone levels are elevated or on the higher side of an ideal range. In response to a determination that the ketone levels are less than (<) 3 mmol/L, the processor may return to 720 to continue to monitor the ketone levels 715. Alternatively, in response to an affirmative determination that ketone levels are greater than (>) 3 mmol/L, the processor may point to a need to increase insulin delivery and proceed to decision block 730.

Depending on the type of diabetes that a user has been diagnosed as having, the control application may implement different responses when the particular user is partaking in a ketogenic diet. For example, a user with Type 2 diabetes may have their bolus dosages reduced, and a user with Type 1 may have an overall reduction in the delivery of insulin. When the user is on a keto diet, the MDA algorithm implemented by the control application may, for example, be operable to reduce a user's TDI by separating out and independently adjusting basal delivery and bolus dosages to make sure that the respective basal deliveries and bolus dosages are delivered according to an appropriate schedule and within an acceptable range. The control application is operable to monitor ketones (via, for example, ketone sensor 196) simultaneously to ensure the user is adhering to the indicated keto diet and is not at risk of hypoglycemia.

For example, at 730, the processor may determine that one or more of the recent glucose (BG) values 713 are greater than 250 mg/dL. In response to a determination that the ketone levels are >3 mmol/L and at least one of the BG values is greater than (>) 250 mg/dL, the processor may be operable, at 737, to cause delivery of a correction insulin dose of x % of TDI (where x is between 3% and 10%) (so as to increase insulin on board or IOB) and generate a prompt on a GUI for the user to increase hydration. Alternatively, at 730, in response to a determination that the ketone levels are >3 mmol/L and none of the BG values is greater than (>) 250 mg/dL, the processor may proceed to 735. At 735, the processor may be operable to cause generation of a prompt for the user to increase hydration and ingest carbohydrates (carbs). After generation of the prompts and/or delivery of the correction insulin dose, the process 700 returns to 720 to continue to monitor the ketone levels.

The examples of FIGS. 6 and 7 may be combined as a single embodiment to enable the system to determine adherence to a chosen diet (i.e., a ketogenic diet or a non-ketogenic diet) as well as provide assistance with the possibility of DKA.

Another process provides monitoring for diet adherence to the ketogenic diet. For example, the controller may confirm diet adherence by monitoring ketone levels and determining if nutritional ketosis has set in. Additionally, adherence to the ketogenic diet or the lack of adherence can be flagged and the appropriate feedback may be provided to the user. In an example, the control application may be operable to ensure compliance with a designated ketogenic diet (i.e., a diet plan set by the user according to the examples described above) based on ketone level measurements provided by the ketone sensor. The designated ketogenic diet from FIG. 2 may also include settings for how strict of a ketone diet the user intends to follow. For example, a strict ketogenic diet may involve consumption of less than 30 grams of carbohydrates a day (with an appropriate range of fat and protein levels to meet caloric needs), while a less strict ketogenic diet may involve consumption of 50 grams of carbohydrates a day with a different range of fat and protein levels to meet caloric needs. In an example, after a user indicates that they are following a ketogenic diet, the user's ketone levels are expected to rise. For example, a typical ketone level increase experienced by a user following (or on or partaking in) a ketogenic diet may be approximately 1.5-3 mmol/L.

Safety Monitoring in Type 2 Users on Drug Delivery Systems and Sodium-Glucose Cotransporter-2 (SGLT2) Inhibitors A system, such as MDA system 100 of FIG. 1, equipped with a continuous ketone sensor and a glucose sensor that implements the process 600 may feasibly provide a warning system for both diabetic ketoacidosis (DKA) and euglycemic diabetic ketoacidosis (euDKA). DKA is a combination of hyperglycemia (e.g., a glucose level greater than 250 mg/dL), acidosis and ketosis. Euglycemic Diabetic Keto Acidosis (euDKA) is a rare condition that may be experienced by Type 2 diabetic patients who use SGLT2 and when the patient partakes in a low carbohydrate diet, and/or alcohol ingestion, and/or after exercising. Other precipitating factors can also include sickness (vomiting, dehydration, viral or bacterial infection) and fasting. The near normal glucose levels seen in euDKA caused by SGLT2 inhibitors results from a balance between endogenous glucose production and renal glucose clearance. Type 1 diabetics may also take SGLT2 inhibitors off label and face euDKA risks as Type 2 diabetics.

In addition to the above steps, additional steps may be implemented based on the determined levels of ketones. For example, ketone levels greater than 10 mmol/L are a sign of impending DKA. The processor, for example, may cause implementation of DKA protocols for prompting the user to seek medical attention or consume hydration and/or electrolytes as well as manage insulin delivery via the drug delivery system to address impending DKA. However, actions may be taken before ketone levels are greater than 10 mmol/L. For example, preventive action can be taken when the ketone levels exceed 5 mmol/L, such as generating prompts for the user to increase hydration, ingest carbohydrates, and adjustments to the MDA to increase the amount of insulin delivered via basal and bolus delivery.

The following is a discussion of example processes for monitoring for euglycemic Diabetic Keto Acidosis (euDKA) by using continuous monitoring of ketone levels with a subcutaneous ketone sensor, a continuous glucose monitor, and exercise monitoring with on board heart rate and accelerometer sensors.

The processes include another example of ketone monitoring and exercise monitoring. In the example, processes, ketone monitoring may be performed by a drug delivery system using an embedded/auxiliary ketone sensor that monitors ketone levels continuously subcutaneously. Exercise is monitored because, in some cases, exercise elevates ketone levels. Exercise monitoring may be performed by using an optional onboard heart rate monitor and accelerometer sensors. Exercise can in some cases elevate ketone levels. The described processes also include euDKA monitoring, in which the ketone levels and glucose levels of a user may be monitored for prompt response to incipient euDKA. Since the drug delivery system processor has access to BG measurement values, the processor may also check for classic DKA.

Drug delivery systems, such as those shown in FIG. 1, may be equipped with a continuous subcutaneous ketone sensor. A concentration of 3-hydroxybutyrate may be determined by a ketone sensor, which may be integrated with a CGM sensor, based on a measurement of the 3-hydroxybutyrate dehydrogenase (3HBDH) enzyme. In some examples, hydrogel membranes have been used to improve ketone concentration and reduce electrode fouling. Ketone levels for nutritional ketosis are summarized in Table 1 above. In other examples, the ketone sensor and the CGM sensor may be integrated within the insulin delivery system (e.g., wearable drug delivery device 102 of FIG. 1) as one physical unit or a combination of units that may be coupled together to form a singular unit.

Figure 8:
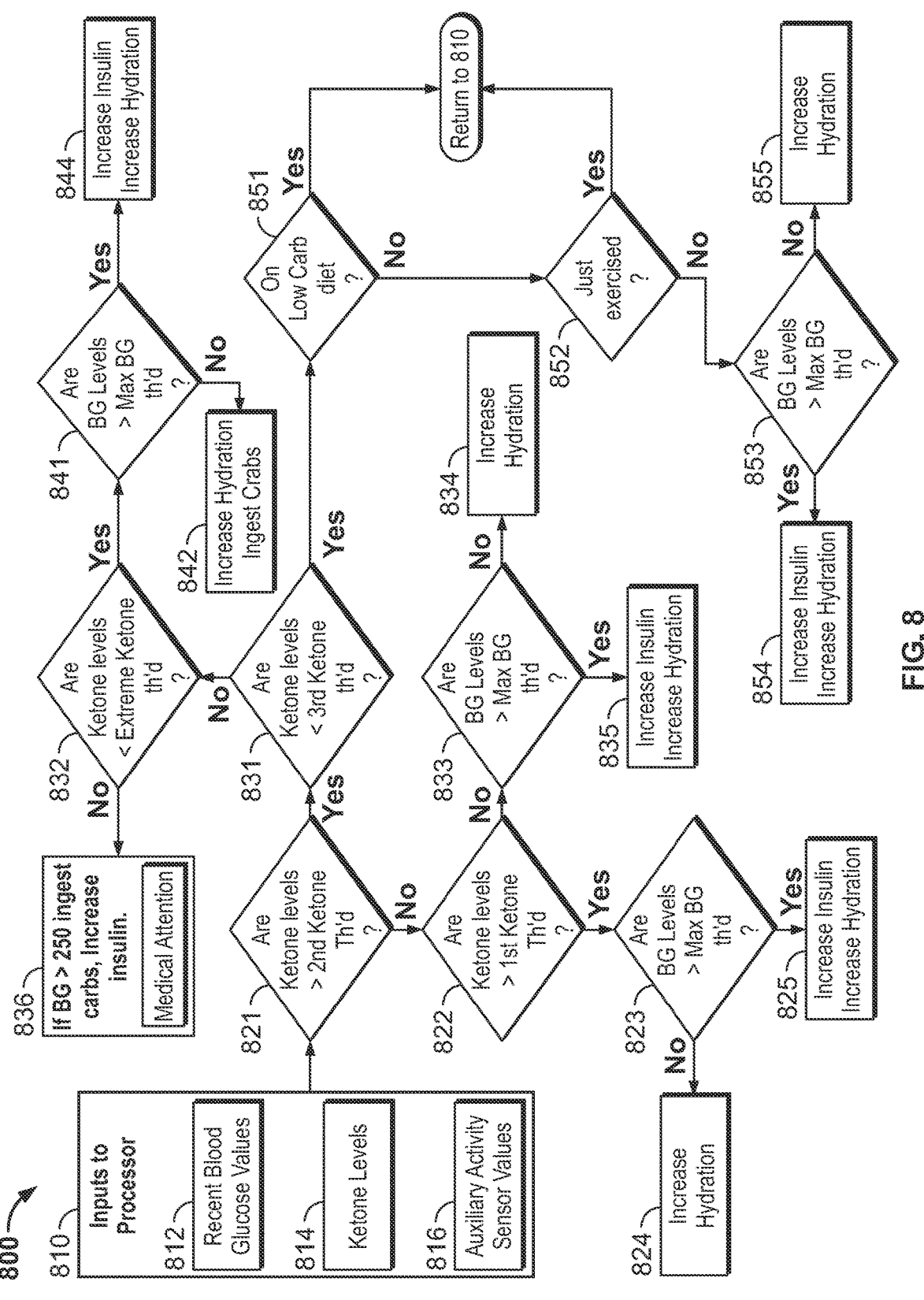
FIG. 8 illustrates a flowchart of another exemplary process for monitoring a user using ketone sensing and activity sensing for DKA and euDKA.

FIG. 8 illustrates a flowchart of an example process for monitoring a user using ketone sensing and activity sensing for DKA. The process 800 of FIG. 8 shows the evaluation of different ketone levels with respect to glucose levels, low carbohydrate diet type, and exercise level with actions taken in response to different evaluation results. The inputs 810 to the processor may be provided by a glucose (BG) sensor, a ketone sensor, and an activity sensor and may include, respectively, recent glucose values 812 (e.g., BG values within the last 15 minutes or the like), ketone levels 814 (e.g., ketone values within the last 30 minutes or the like), and auxiliary activity sensor values 816 (e.g., heart rate in last 5 minutes, blood oxygen level in last 10 minutes, and the like). When all of those sensors are communicatively coupled to a controller, such as 104 of FIG. 1, no input is needed from the user. However, different actions or interpretations by the processor may be confirmed with user inputs/questions via a GUI. For example, different evaluation paths may be followed based on an evaluation of the respective recent glucose values 812, ketone levels 814, and auxiliary activity sensor values 816. These respective values may be evaluated beginning at step 821.

At 821, the processor may determine whether the user's ketone levels are greater than a second ketone threshold, such as 3 mmol/L, or the like. If the determination is "Yes", the user's ketone levels are greater than the second ketone threshold, the process 800 may proceed to 831 at which the processor may determine whether the user's ketone levels are less than a third ketone threshold, such as 5 mmol/L or the like. The second ketone threshold is less than the third ketone level. If the determination is "Yes", the user's ketone levels are less than the third ketone threshold, the process 800 may proceed to 851 at which the processor may generate a prompt on a GUI inquiring whether the user is on a low carbohydrate (carb) diet. If the processor receives an input at 851 confirming the user is on the low carbohydrate diet, the process 800 may return to 810. Alternatively, at 851, if the processor receives an input at 851 indicating that the user is not on a low carbohydrate diet, the process 800 may proceed to 852. At 852, the processor may generate a prompt on a GUI inquiring whether the user just exercised. If the response to the GUI query at 852 is "Yes," the process 800 may return to 810. Alternatively, if the response to the GUI query at 852 is "No, have not exercised," the process 800 may proceed to 853. At 853, the processor may determine whether the user's BG levels are greater than a maximum BG level, such as 250 mg/dL or the like. In response to the determination that the user's BG levels are greater than a maximum BG level (i.e., a "Yes" at 853), the processor may generate a notification, such as a window on a GUI, recommending that the user increase their hydration as well as, either automatically or upon user confirmation, cause a wearable drug delivery device to deliver increased insulin. Conversely, in response to the determination that the user's BG levels are less than a maximum BG level (i.e., a "No" at 853), the processor may generate a notification, such as a window on a GUI, recommending that the user increase their hydration.

Returning to 831, in response to a determination that the user's ketone levels are not below the third ketone threshold, the process 800 may proceed to 832. At 832, the processor may determine whether the user's ketone levels are less than an extreme ketone threshold. If the determination is "No" or "the user's ketone levels are greater than an extreme ketone threshold," the processor may cause an alert, including audio signals as well as a visual notification in addition to the GUI prompt for the user to seek medical attention. Additionally, in a smartphone implementation example, the processor may be operable to cause a calling application of the smartphone to call a healthcare provider or emergency service provider (e.g., by dialing "911" or the like). In the case of ketone levels greater than 10 mmol/L (which is an indication of diabetic ketoacidosis), a notification may be provided for the user to seek medical attention, In addition, should the user's BG levels be greater than, for example, 250 mg/dL (which is a maximum BG threshold), the processor may cause the delivery of insulin (to lower the BG levels) by a wearable drug delivery device (such as 102 in FIG. 1 and a recommendation for the user to ingest carbohydrates (to reduce the ketone levels). For example, a healthcare provider may administer electrolytes, glucagon, carbohydrates and provide hydration. Alternatively, if at 832, the determination is "Yes", the user's ketone levels are less than an extreme ketone threshold, the process 800 may proceed to 841.

At 841, the processor evaluates the user's glucose levels with reference to a maximum BG threshold, which may be dependent on each respective user. In the example of FIG. 8, the maximum BG threshold is 250 mg/dL. If a user's glucose value is greater than the maximum BG threshold (e.g., 250 mg/dL) (i.e., "YES", the BG level is greater than the maximum BG threshold), the processor may cause a notification to be generated on the GUI for the user to increase their hydration and the processor may send a signal to the wearable drug delivery device causing an increase in the delivery of insulin to the user (e.g., via a correction bolus or via a temporary increase to the user's basal rate). Alternatively, if the determination at 841 is "No, the BG level is not greater than the maximum BG threshold, the processor may cause a notification to be generated on the GUI for the user to increase their hydration and ingest carbohydrates.

Returning to 821, if the determination by the processor is "No," the ketone levels are not greater than the second ketone threshold, the process 800 proceeds to 822. At 822, the processor evaluates the ketone levels 814 measured by the ketone sensor with respect to a first ketone threshold. The first ketone threshold is less than the second ketone level.

If the result of the evaluation or the determination at 822 is "Yes," the ketone levels are greater than the first ketone threshold, the process 800 proceeds to 823. At 823, the processor evaluates the user's glucose levels with reference to the maximum BG threshold, and if the result of the evaluation is the user's glucose levels are less than the maximum BG threshold (i.e., "NO"), the processor generates a prompt 824 on the GUI for the user to increase hydration. Alternatively, if the result of the evaluation is the user's glucose levels are greater than the maximum BG threshold (i.e., "Yes"), the processor generates a prompt 825 on the GUI for the user to increase hydration and the processor may send a signal to the wearable drug delivery device causing an increase in the delivery of insulin to the user.

Returning to 822, if the result of the evaluation or the determination at 822 is "No," the ketone levels are not greater than the first ketone threshold, the process 800 proceeds to 833.

At 833, the processor still takes the precaution to evaluate the user's glucose values with respect to the maximum BG threshold. If, at 833, the result of the evaluation by the processor is the user's glucose levels are less than the maximum BG threshold (i.e., "NO"), the processor generates a prompt 834 on the GUI for the user to increase hydration. Alternatively, if the result of the evaluation is the user's glucose levels are greater than the maximum BG threshold (i.e., "Yes"), the processor generates a prompt 835 on the GUI for the user to increase hydration and the processor may send a signal to the wearable drug delivery device causing an increase in the delivery of insulin to the user.

Recommendations such as to increase hydration; ingest carbs; and/or seek medical attention may be output via the GUI. The processor may be further operable to adjust medicament delivery to the user automatically without alerting the user.

For example, in an operational example, the processor may obtain ketone levels of a user either from the inputs to the processor 810 or by accessing a memory device storing the ketone levels. The processor may be operable to evaluate the obtained ketone levels with reference to a plurality of ketone thresholds. Based on the result of the evaluation, the processor may provide an indication for a further action by the processor, such as the further actions of presenting a notification to seek medical attention at 836, noting in an MDA/ADD/AP application that the user is on a low carbohydrate diet 851, or the user exercised 852. For example, the processor may adjust settings in the MDA/ADD/AP application to indicate that the user is on a low carbohydrate diet or the user exercised and the adjusting settings may be operable to compensate for the low carbohydrate diet (e.g., reducing bolus dosage amounts and the like) or the user's participation in exercise (e.g., a setting to deal with increased ketones and decreased glucose levels).

The processor based on the evaluation of a user's ketone levels and an evaluation of the user's glucose level(s) may be further operable to generate additional indications in case the user is potentially experiencing euDKA. Based on the additional indications, the processor may be operable to present a notification to ingest carbohydrates, such as at 836 and 842, presenting a notification to increase hydration, such as at 824, 825, 835, 842, 844, 854, and 855, generating a signal to increase insulin delivery, such as 825, 835, 836, 844, and 854, or a combination thereof, such as 825, 835, 836, 842, 844, and 854.

In the example process 800, the processor may determine that the user's BG levels may be in range of the target setpoint, but the user's ketone levels might be higher than normal for the particular user. This condition may be in response to the user's use of SGLT2. In addition, if the user is taking SGLT2 and insulin, the user may go into higher ketosis states (e.g., ketones greater than 3 mmol/L) and yet the user's BG is in a normal range, so there is a risk of euDKA for the user.

Another process provides monitoring for hypoglycemia. Hypoglycemia monitoring may include a control application implementing a reduction in insulin dosages to safeguard against hypoglycemia. In addition, the control application may monitor trends in a user's glucose levels and/or insulin on board levels and based on the monitored trends, take actions to prevent occurrences of hypoglycemia. For example, based on the monitored trends, the control application may suspend insulin or alerting the user to ingest fast acting carbohydrates. Onboard (e.g., wearable, and wireless communication-equipped) activity sensors, when available or when coupled to a controller, provide additional insights into projected glucose trends of the user. For example, exercise monitoring may be accomplished via auxiliary activity sensors, such as a heart rate monitor and/or accelerometer. The data from one or both of these sensors may provide data related to an activity level and type of exercise performed by the patient. For example, the analyte sensor(s) may be a snap fit sensor unit including heart rate and accelerometer sensors for exercise monitoring and type of exercise and intensity level. In other embodiments, activity data from fitness devices, such as a Fitbit® or the like, may be used.

Figure 9:
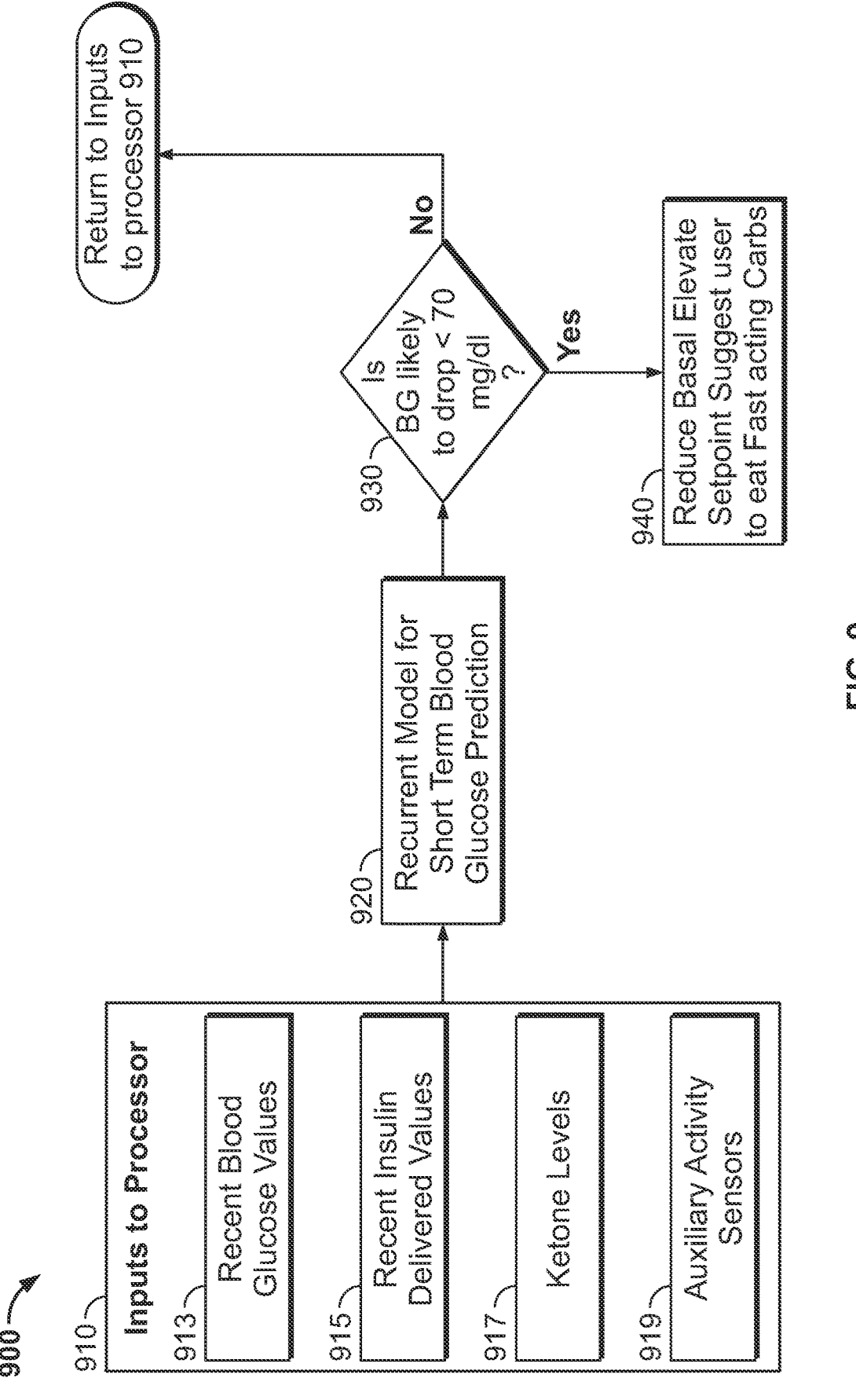
FIG. 9 illustrates a flowchart of a process for monitoring a user for indications of hypoglycemia when the user is adhering to a ketogenic diet.

FIG. 9 illustrates a flowchart of a process for monitoring for hypoglycemia. The processor of drug delivery system may be operable to monitor a user for hypoglycemia. For example, inputs to processor 910 may include at least one or more of recent glucose values 913, recent insulin delivered values 915, ketone levels 917 or auxiliary activity sensors 919. Trends in the glucose and the current insulin on board can be used to predict if the glucose is going to fall rapidly in the next half hour at 920 (e.g., below a minimum target setpoint, for example, 70 mg/dL). Utilizing a recurrent neural network (RNN) model that accepts the inputs 913, 915, 917 and 919, the processor evaluates the glucose prediction from 920 at 930. For example, the processor, for example, using a recurrent model may determine a trend of the predicted glucose values over time, such as a rate of change or the like, to determine a projected value of the predicted glucose values over a short term. The short term may be a number of hours, such as 3-6, or the like.

Returning to back to the discussion of FIG. 9 at 930, if the determination is YES, a fall to below a minimum target setpoint or a minimum glucose threshold value is projected, the processor may proceed to 940 at which the processor may generate a prompt on a GUI for the user to ingest carbs, elevate the minimum target setpoint or a minimum glucose threshold value, and the processor may also reduce or suspend basal insulin. Conversely, if NO, a fall below the minimum target setpoint or a minimum glucose threshold value is not projected, the processor may return to 910 to receive inputs.

The ADD sensor subsystem may, for example, also be equipped with other auxiliary sensors for activity monitoring including heart rate, accelerometer, skin conductance. These sensors may detect exercise and respond by lowering basal insulin at the time of exercise, elevate glucose setpoint in the Drug delivery system, suggest hydration. Glucose levels may, for example, be predicted using a recurrent neural network to alter basal insulin. The process 900 of FIG. 9 depicts hypoglycemia prediction and alerts.

Figure 10:
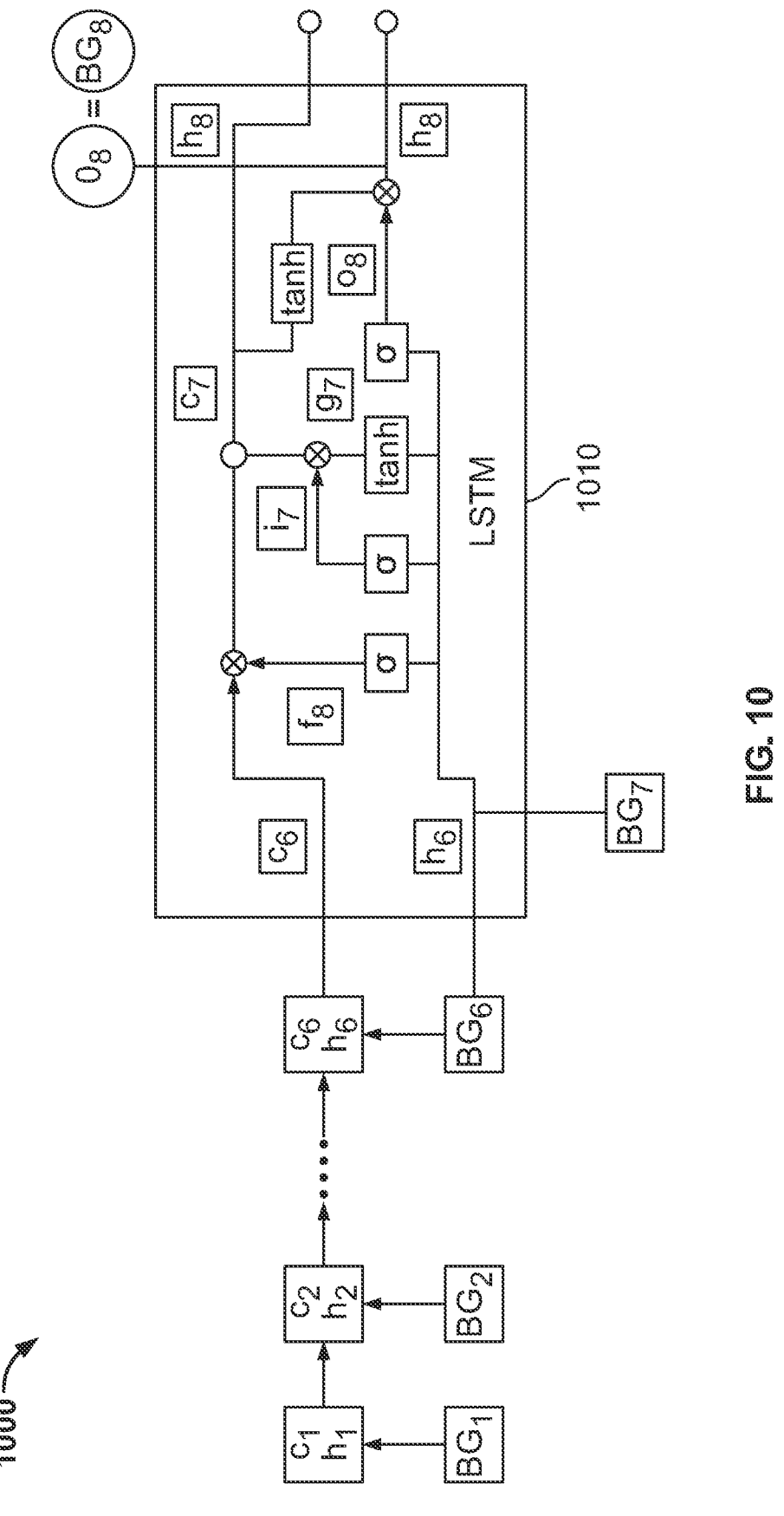
FIG. 10 illustrates a high-level example of a machine learning process for predicting a future glucose measurement value.

A brief discussion of an RNN implementation may be beneficial. FIG. 10 illustrates an example of a recurrent neural network (RNN) in the form of a long short-term memory being trained to estimate or predict future glucose measurement values based on past glucose measurement values. As an example of glucose prediction, we may have a sequence of values that span 30 minutes of data (7 data points spread at 5 minutes). The RNN can be used to predict the glucose measurement value after 30 minutes. For example, given a sequence of glucose measurement values BG1 through BG7, the RNN may be trained to predict a later glucose measurement value, such as BG8. In the example of FIG. 4D, the glucose measurement values: BG1, BG2, BG3, BG4, BG5, BG6, BG7 may cause the RNN to output BG8. The BG8 value may be used in subsequent training. For example, a typical training sequence may resemble:

BG1, BG2, BG3, BG4, BG5, BG6, BG7->output BG8;
BG2, BG3, BG4, BG5, BG6, BG7, BG8->output BG9;
BG3, BG4, BG5, BG6, BG7, BG8, BG9->output BG10;
. . .
BG18, BG19, BG20, BG21, BG22, BG23, BG24->output BG25.

FIG. 10 shows an example LSTM type of recurrent neural network being trained with a sequence of 7 glucose measurement values ($BG_1$ to $BG_7$) to predict the $8^{th}$ value ($BG_8$). The above training framework may be extended with an input of greater than 7 glucose measurement values and an output greater than one glucose measurement value, for example, 2-10 estimated glucose measurement values may be output from the RNN. Also, the sequence of predictions may include additional input variables other than glucose measurement values. For example, the additional input variables may include inputs such as a stress value, an insulin dose and carbohydrate values to predict the sequence of glucose measurement values. The LSTM implementation is effective to mitigate and even eliminate the vanishing gradient problem that may occur when gradient-based learning methods and backpropagation is utilized. In the example illustrated in FIG. 10, the long short-term memory (LSTM) 1010, may predict a user's glucose value after, for example, 30 minutes, 40 minutes, 60 minutes, or the like. The LSTM may be trained with sequences of 7 contiguous values and the LSTM is operable to learn the 8th value (which may be 30 minutes in the future) and more values.

As shown above, the represented training framework may be extended with an input of greater than 7 values and an output greater than one measurement. Also, the sequence predictions can include other variables such as a stress value, an insulin dose and carbohydrate values to predict the glucose sequence.

Software related implementations of the techniques described herein, such as the processes examples described with reference to the above discussion and figures may include, but are not limited to, firmware, application specific software, or any other type of computer readable instructions that may be executed by one or more processors. The computer readable instructions may be provided via non-transitory computer-readable media. The various elements of the processes described with reference to the figures may be implemented in devices, apparatuses or systems that may include various hardware elements, software elements, or a combination of both. Examples of hardware elements may include structural members, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, processes, procedures, software interfaces, application program interfaces (API), instruction sets, computing code, computer code, code segments, computer code segments, words, values, symbols, or any combination thereof.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but the intention is that additions and modifications to what was expressly described herein are also included within the scope of the disclosed examples. Moreover, it is to be understood that the features of the numerous examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, novel subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible considering this disclosure. It is intended that the scope of the present disclosure be limited not by this detailed description, but by the claims appended hereto. Future filed applications claiming priority to this application may claim the disclosed subject matter in a different manner and may include any set of one or more features as variously disclosed or otherwise demonstrated herein.

What is claimed is:

1. A drug delivery system, comprising:
   a processor operable to execute programming instructions;
   a user interface including a touchscreen display and user input circuitry;
   a memory operable to store the programming instructions; and
   a communication circuitry coupled to the processor and operable to receive and transmit communication signals, wherein the processor is operable to:
      receive an indication that a user is starting a ketogenic diet;
      retrieve a baseline total daily insulin value;
      calculate a keto total daily insulin value using the retrieved baseline total daily insulin value; and
      utilize the keto total daily insulin value in the calculation of a keto basal dosage of insulin or a keto bolus dosage of insulin.

2. The drug delivery system of claim 1, further comprising:
   a glucose sensor operable to transmit glucose measurement values during a period of time;
   a ketone sensor operable to transmit ketone levels, wherein the communication circuitry is operable to receive transmissions of the glucose measurement values and the ketone values; and
   the processor is operable to:
      receive a glucose measurement value during a post prandial portion of the period of time and during a nighttime portion of the period of time;
      receive a ketone level during the post prandial portion of the period of time;
      calculate a new total daily insulin value based on the received glucose measurement value and the received ketone level; and
      adapt the keto basal dosage and the keto bolus dosage based on the new total daily insulin.

3. The drug delivery system of claim 1, wherein the processor is further operable to:
   receive a glucose measurement value during a post prandial portion of the period of time and during a nighttime portion of the period of time;
   receive a ketone level during the post prandial portion of the period of time;
   calculate a new total daily insulin value based on the received glucose measurement value and the received ketone level; and
   adapt the keto basal dosage and the keto bolus dosage based on the new total daily insulin.

4. The drug delivery system of claim 1, wherein the processor is further operable to:
   determine, based on an input received from a graphical user interface presenting on the touchscreen display, whether the user is starting a ketogenic diet; and
   in response to the determination that the user is starting the ketogenic diet, determine a time period over which the user is expected to continue the ketogenic diet.

5. The drug delivery system of claim 4, wherein the processor is further operable to:
   in response to the determination that the user is participating in the diet cycle, generating a prompt in the graphical user interface presented on the touchscreen display, whether the ketogenic diet is on fixed days of the week; and
   in response to an indication that the ketogenic diet is on fixed days of the week, present an interactive calendar with days of the week for selection by a user.

6. The drug delivery system of claim 1, wherein the processor, when calculating the keto total daily insulin value using the retrieved baseline total daily insulin value, is further operable to:

multiply the retrieved baseline total daily insulin value by a keto day factor, wherein the keto day factor is less than 1.

7. The drug delivery system of claim 1, wherein the processor is further operable to:

receive an indication that a user is starting a non-keto-genic diet;

retrieve the new total daily insulin value, which is a keto day total daily insulin value;

calculate a non-keto total daily insulin value using the keto day total daily insulin value; and utilize the non-keto total daily insulin value in the calculation of a non-keto basal dosage of insulin or a non-keto bolus dosage of insulin.

8. The drug delivery system of claim 7, wherein the processor, when calculating the non-keto total daily insulin value using the keto day total daily insulin value, is further operable to:

multiply the keto day total daily insulin value by a non-keto day factor, wherein the non-keto day factor is greater than 1.

9. A drug delivery system, comprising:

a processor operable to execute programming instructions;

a user interface including a display and user input circuitry;

a memory operable to store the programming instructions; and communication circuitry coupled to the processor and is operable to receive and transmit communication signals, wherein the processor is operable to:

receive ketone levels from a ketone sensor;

generate a prompt on the user interface inquiring whether a user's diet for a time period is a keto diet or a non-keto diet; and based on the received ketone levels of the user, generate an indication of whether the user is adhering to a keto diet.

10. The drug delivery system of claim 9, wherein the processor is further operable to:

in response to a response to the prompt indicating the user's diet for the time period is a keto diet, determine whether a user's post prandial ketone levels received from a ketone sensor are greater than a first ketone value and less than a second ketone value; and in response to the user's post ketone levels being within the first ketone value and the second ketone value, generate an adherence indication.

11. The drug delivery system of claim 9, wherein the processor is further operable to:

in response to a response to the prompt indicating the user's diet for the time period is not a keto diet, determine whether a user's post prandial ketone levels received from a ketone sensor are less than the first ketone value; and in response to the user's post ketone levels being less than the first ketone value, generate an adherence indication.

12. The drug delivery system of claim 11, wherein the processor is further operable to:

in response to the user's post prandial ketone levels being greater than the first ketone value, send a notice to a user device with query confirming the time period is a keto time period.

13. The drug delivery system of claim 9, wherein the processor is further operable to:

in response to the user's post prandial ketone levels being outside a range of the first ketone value and the second ketone value, send a notice to a user device with query confirming today is a keto time period.

14. The drug delivery system of claim 9, wherein:

the first ketone value is approximately 0.5 mmol/L and the second ketone value is approximately 5 mmol/L.

15. The drug delivery system of claim 9, wherein the processor is further operable to:

receive a glucose value from a glucose sensor;

determine whether the received ketone levels are greater than a first ketone value;

in response to the received ketone levels being greater than the first ketone value, determine whether the received glucose value exceeds a predetermined glucose value; and in response to the received glucose value exceeding the predetermined glucose value, increase a delivery of insulin and generate a prompt on the touchscreen display for the user to increase consumption of liquids, or in response to the received glucose value being less than the predetermined glucose value, generate a prompt on the touchscreen display for the user to increase consumption of liquids and to ingest carbohydrates.

16. A controller of a drug delivery system, comprising:

a processor operable to execute programming instructions;

a memory operable to store the programming instructions; and communication circuitry coupled to the processor and be operable to receive and transmit communication signals, wherein the processor, when executing the programming instructions, is operable to:

obtain ketone levels of a user;

evaluate the obtained ketone levels with reference to a plurality of ketone thresholds;

based on the result of the evaluation, selecting a further action to be performed, wherein the further action is at least one of generating a notification to seek medical attention, generating a notification to ingest carbohydrates, generating a notification that the processor will increase drug delivery, or a combination thereof.

17. The controller of the drug delivery system of claim 16, wherein:

the plurality of ketone thresholds include a first ketone threshold, a second ketone threshold, a third ketone threshold and an extreme ketone threshold, and the processor, when evaluating the obtained ketone levels with reference to the plurality of ketone thresholds, is further operable to:

compare a latest ketone value of the obtained ketone levels to a second ketone threshold of the plurality of ketone thresholds;

in response to the latest ketone value being greater than the first ketone threshold, compare the latest ketone value to a third ketone threshold;

in response to the latest ketone value being greater than the third ketone threshold, compare the latest ketone value to an extreme ketone threshold; and in response to the latest ketone value being greater than the extreme ketone threshold, selecting generating the notification the user is to seek medical attention as the selected further action.

18. The controller of the drug delivery system of claim 16, wherein the processor, when executing the programming instructions, is further operable to:

obtain glucose levels of the user;

evaluate the glucose level to a maximum glucose threshold;

based on the evaluation of the obtained ketone levels with reference to the plurality of ketone thresholds and the evaluation of the glucose level to the maximum glucose threshold, provide an indication for additional action by the processor.

19. The controller of the drug delivery system of claim 16, wherein the processor is further operable to:

determine the user is experiencing ketoacidosis; and increase delivery of insulin.

20. The controller of the drug delivery system of claim 18, wherein the processor is further operable to:

determine whether the user is experiencing diabetic ketoacidosis;

in response to the determination indicating a drop below a minimum glucose threshold value, perform at least one of:

generate a prompt on the user interface for the user to ingest carbs, elevate a minimum target setpoint or the minimum glucose threshold value, or reduce a basal rate of drug delivery.

* * * * *